United States Patent
Weiner et al.

(10) Patent No.: US 6,274,136 B1
(45) Date of Patent: Aug. 14, 2001

(54) CONSTRUCTION AND USE OF GENES ENCODING PATHOGENIC EPITOPES FOR TREATMENT OF AUTOIMMUNE DISEASE

(75) Inventors: Leslie P. Weiner, Los Angeles; Minnie McMillan, Bradbury, both of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 08/654,737

(22) Filed: May 29, 1996

(51) Int. Cl.[7] .......................... A61K 48/00; C12N 15/00; C12N 7/00
(52) U.S. Cl. .................. 424/93.21; 424/93.2; 424/199.1; 514/44; 435/325; 435/252.1
(58) Field of Search ............................... 424/199.1, 93.2, 424/93.21; 514/44; 435/325, 252.1

(56) References Cited

U.S. PATENT DOCUMENTS

| | | |
|---|---|---|
| 5,264,618 | 11/1993 | Felgner et al. ..................... 560/224 |
| 5,399,346 | 3/1995 | Anderson et al. ................. 424/93.21 |
| 5,459,127 | 10/1995 | Felgner et al. ............................ 514/7 |
| 5,580,859 | 12/1996 | Felgner et al. .......................... 514/44 |
| 5,589,466 | 12/1996 | Felgner et al. .......................... 514/44 |
| 5,716,826 * | 2/1998 | Gruber et al. ..................... 435/320.1 |

OTHER PUBLICATIONS

Barnett et al. (Feb. 1996) Journal of Immunology;64, 163–173.*

Lemay et al. (Sep. 1989) Journal of Biological Chemistry; 264 (26), 15620–15623.*

Kalden et al. (1998) Advances in Immunology; 68, 333–418.*

Miller et al. (Aug. 1994) Immunology Today; 15 (8), 356–360.*

Willenborg et al. (Feb. 1998) Immunology and Cell Biology; 76 (1), 91–103.*

Crystal, Ronald G (Oct. 1995) Science; 270, 404–410.*

Al–Sabbagh et al., "Antigen–driven tissue–specific suppression following oral tolerance: orally administered myelin basic protein suppresses proteolipid protein–induced experimental autoimmune encephalomyelitis in the SJL mouse," Eur. J. Immunology, 24:9, pp. 2104–2109, (Sep. 1994).

Donnelly et al., "Immunization with DNA," J. of Immunological Methods, 176, pp. 145–152, (Aug. 29, 1994).

Fynan et al., "DNA Vaccines: Protective immunizations by parenteral, mucosal, and gene gun inoculations," Proc. Natl. Acad. Sci., 90, pp. 11478–11482, (Dec. 1993).

Gaur et al., "Amelioration of autoimmune encephalomyelitis by myelin basic protein synthetic peptide–induced anergy," Science, 258:5087, pp. 1491–1494, (Nov. 27, 1992).

Javed et al., "Exquisite peptide specificity of oral tolerance in experimental autoimmune encephalomyelitis,", J. of Immunology, 155:3, pp. 1599–1605 (Aug. 1, 1995).

Wraith, D.C., "Induction of antigen–specific unresponsiveness with synthetic peptides: specific immunotherapy for treatment of allergic and autoimmune conditions," International Archives of Allergy and Immunology, 108:4, pp. 355–359, (Dec. 1995).

Yu et al., "A predictable sequential determinant spreading cascade invariably accompanies progression of experimental autoimmune encephalomyelitis: a basis for peptide–specific therapy after onset of clinical disease," J. of Experimental Medicine, 183:4, pp. 1777–1788, (Apr. 1, 1996).

* cited by examiner

Primary Examiner—Karen M. Hauda
Assistant Examiner—Anne Marie S. Beckerleg
(74) Attorney, Agent, or Firm—McCutchen, Doyle, Brown & Enersen LLP

(57) ABSTRACT

The present invention relates to the application of genetic engineering to provide a treatment of autoimmune disease. This is achieved preferably through the introduction of one or more recombinant genes encoding self antigens which are the target of an autoimmune response. In particular the invention provides a method of designing and constructing a gene encoding an encephalogenic epitope of proteolipid protein, and to the in vivo expression of the gene product by a recombinant retroviral vector. The expression and secretion of the encephalogenic epitope ameliorates the histopathological and clinical characteristics of experimental autoimmune encephalomyelitis (EAE) in the mouse model for multiple sclerosis (MS).

**21 Claims, 15 Dr

```
TTTGAAAGAC CCCACCCGTA GGTGGCAAGC TAGCTTAAGT AACGCCACTT TGCAAGGCAT  60
GGAAAAATAC ATAACTGAGA ATAGAAAAGT TCAGATCAAG GTCAGGAACA AAGAAACAGC 120
TGAATACCAA ACAGGATATC TGTGGTAAGC GGTTCCTGCC CCGGCTCAGG GCCAAGAACA 180
GATGAGACAG CTGAGTGATG GGCCAAACAG GATATCTGTG GTAAGCAGTT CCTGCCCCGG 240
CTCGGGGCCA AGAACAGATG GTCCCCAGAT GCGGTCCAGC CCTCAGCAGT TTCTAGTGAA 300
TCATCAGATG TTTCCAGGGT GCCCCAAGGA CCTGAAAATG ACCCTGTACC TTATTTGAAC 360
TAACCAATCA GTTCGCTTCT CGCTTCTGTT CGCGCGCTTC CGCTCTCCGA GCTCAATAAA 420
AGAGCCCACA ACCCCTCACT CGGCGCGCCA GTCTTCGAT AGACTGCGTC GCCCGGGTAC 480
CCGTATTCCC AATAAAGCCT CTTGCTGTTT GCATCCGAAT CGTGGTCTCG CTGTTCCTTG 540
GGAGGGTCTC CTCTGAGTGA TTGACTACCC ACGACGGGGG TCTTTCATTT GGGGGCTCGT 600
CCGGGATTTG GAGACCCCTG CCCAGGGACC ACCGACCCAC CACCGGGAGG TAAGCTGGCC 660
AGCAACTTAT CTGTGTCTGT CCGATTGTCT AGTGTCTATG TTTGATGTTA TGCGCCTGCG 720
TCTGTACTAG TTAGCTAACT AGCTCTGTAT CTGGCGGACC CGTGGTGGAA CTGACGAGTT 780
CTGAACACCC GGCCGCAACC CTGGGAGACG TCCCAGGGAC TTTGGGGGCC GTTTTGTGG 840
CCCGACCTGA GGAAGGGAGT CGATGTGGAA TCCGACCCCG TCAGGATATG TGGTTCTGGT 900
AGGAGACGAG AACCTAAAAC AGTTCCCGCC TCCGTCTGAA TTTTTGCTTT CGGTTTGGAA 960
CCGAAGCCGC GCGTCTTGTC TGCTGCAGCG CTGCAGCATC GTTCTGTGTT GTCTCTGTCT 1020
GACTGTGTTT CTGTATTTGT CTGAAAATTA GGGCCAGACT GTTACCACTC CCTTAAGTTT 1080
GACCTTAGGT CACTGGAAAG ATGTCGAGCG GATCGCTCAC AACCAGTCGG TAGATGTCAA 1140
GAAGAGACGT TGGGTTACCT TCTGCTCTGC AGAATGGCCA ACCTTTAACG TCGGATGGCC 1200
GCGAGACGGC ACCTTTAACC GAGACCTCAT CACCCAGGTT AAGATCAAGG TCTTTTCACC 1260
TGGCCCGCAT GGACACCCAG ACCAGGTCCC CTACATCGTG ACCTGGGAAG CCTTGGCTTT 1320
TGACCCCCCT CCCTGGGTCA AGCCCTTTGT ACACCCTAAG CCTCCGCCTC CTCTTCCTCC 1380
ATCCGCCCCG TCTCTCCCCC TTGAACCTCC TCGTTCGACC CCGCCTCGAT CCTCCCTTTA 1440
TCCAGCCCTC ACTCCTTCTC TAGGCGCCGG AATTCGCGGC CGCTACGTAG TCGACTCGCT 1500
GTGGAATGTG TGTCAGTTAG GGTGTGGAAA GTCCCCAGGC TCCCCAGCAG GCAGAAGTAT 1560
GCAAAGCATG CATCTCAATT AGTCAGCAAC CAGGTGTGGA AAGTCCCCAG GCTCCCCAGC 1620
AGGCAGAAGT ATGCAAAGCA TGCATCTCAA TTAGTCAGCA ACCATAGTCC GCCCCTAAC 1680
TCCGCCCATC CCGCCCCTAA CTCCGCCCAG TTCCGCCCAT TCTCCGCCCC ATGGCTGACT 1740
AATTTTTTTT ATTTATGCAG AGGCCGAGGC CGCCTCGGCC TCTGAGCTAT TCCAGAAGTA 1800
GTGAGGAGGC TTTTTTGGAG GCCTAGGCTT TTGCAAAAAG CTCGAAGATC AATTCCGATC 1860
TGATCAAGAG ACAGGATGAG GATCGTTTCG CATGATTGAA CAAGATGGAT TGCACGCAGG 1920
TTCTCCGGCC GCTTGGGTGG AGAGGCTATT CGGCTATGAC TGGGCACAAC AGACAATCGG 1980
CTGCTCTGAT GCCGCCGTGT TCCGGCTGTC AGCGCAGGGG CGCCCGGTTC TTTTTGTCAA 2040
GACCGACCTG TCCGGTGCCC TGAATGAACT GCAGGACGAG GCAGCGCGGC TATCGTGGCT 2100
GGCCACGACG GGCGTTCCTT GCGCAGCTGT GCTCGACGTT GTCACTGAAG CGGGAAGGGA 2160
CTGGCTGCTA TTGGGCGAAG TGCCGGGGCA GGATCTCCTG TCATCTCACC TTGCTCCTGC 2220
CGAGAAAGTA TCCATCATGG CTGATGCAAT GCGGCGGCTG CATACGCTTG ATCCGGCTAC 2280
CTGCCCATTC GACCACCAAG CGAAACATCG CATCGAGCGA GCACGTACTC GGATGGAAGC 2340
CGGTCTTGTC GATCAGGATG ATCTGGACGA AGAGCATCAG GGCTCGCGC CAGCCGAACT 2400
GTTCGCCAGG CTCAAGGCGC GCATGCCCGA CGGCGAGGAT CTCGTCGTGA CCCATGGCGA 2460
TGCCTGCTTG CCGAATATCA TGGTGGAAAA TGGCCGCTTT TCTGGATTCA TCGACTGTGG 2520
CCGGCTGGGT GTGGCGGACC GCTATCAGGA CATAGCGTTG GCTACCCGTG ATATTGCTGA 2580
AGAGCTTGGC GGCGAATGGG CTGACCGCTT CCTCGTGCTT TACGGTATCG CCGCTCCCGA 2640
TTCGCAGCGC ATCGCCTTCT ATCGCCTTCT TGACGAGTTC TTCTGAGCGG GACTCTGGGG 2700
TTCGTCGAGA AGCTTGGGCC CATCGATAAA ATAAAAGATT TTATTTAGTC TCCAGAAAAA 2760
GGGGGGAATG AAAGACCCCA CCTGTAGGTT TGGCAAGCTA GCTTAAGTAA CGCCATTTTG 2820
CAAGGCATGG AAAAATACAT AACTGAGAAT AGAGAAGTTC AGATCAAGGT CAGGAACAGA 2880
TGGAACAGCT GAATATGGGC CAAACAGGAT ATCTGTGGTA AGCAGTTCCT GCCCCGGCTC 2940
AGGGCCAAGA ACAGATGGAA CAGCTGAATA TGGGCCAAAC AGGATATCTG TGGTAAGCAG 3000
TTCCTGCCCC GGCTCAGGGC CAAGAACAGA TGGTCCCCAG ATGCGGTCCA GCCCTCAGCA 3060
GTTTCTAGAG AACCATCAGA TGTTTCCAGG GTGCCCCAAG GACCTGAAAT GACCCTGTGC 3120
CTTATTTGAA CTAACCAATC AGTTCGCTTC TCGCTTCTGT TCGCGCGCTT CTGCTCCCCG 3180
AGCTCAATAA AAGAGCCCAC AACCCCTCAC TCGGGGCGCC AGTCCTCCGA TTGACTGAGT 3240
CGCCCGGGTA CCCGTGTATC CAATAAACCC TCTTGCAGTT GCATCCGACT TGTGGTCTCG 3300
```

*FIG. 2B-1.*

```
CTGTTCCTTG GGAGGGTCTC CTCTGAGTGA TTGACTACCC GTCAGCGGGG GTCTTTCATT 3360
TGGGGGCTCG TCCGGGATCG GGAGACCCCT GCCCAGGGAC CACCGACCCA CCACCGGGAG 3420
GTAAGCTGGC TGCCTCGCGC GTTTCGGTGA TGACGGTGAA AACCTCTGAC ACATGCAGCT 3480
CCCGGAGACG GTCACAGCTT GTCTGTAAGC GGATGCCGGG AGCAGACAAG CCCGTCAGGG 3540
CGCGTCAGCG GGTGTTGGCG GGTGTCGGGG CGCAGCCATG ACCCAGTCAC GTAGCGATAG 3600
CGGAGTGTAT ACTGGCTTAA CTATGCGGCA TCAGAGCAGA TTGTACTGAG AGTGCACCAT 3660
ATGCGGTGTG AAATACCGCA CAGATGCGTA AGGAGAAAAT ACCGCATCAG GCGCTCTTCC 3720
GCTTCCTCGC TCACTGACTC GCTGCGCTCG GTCGTTCGGC TGCGGCGAGC GGTATCAGCT 3780
CACTCAAAGG CGGTAATACG GTTATCCACA GAATCAGGGG ATAACGCAGG AAAGAACATG 3840
TGAGCAAAAG GCCAGCAAAA GGCCAGGAAC CGTAAAAAGG CCGCGTTGCT GGCGTTTTTC 3900
CATAGGCTCC GCCCCCCTGA CGAGCATCAC AAAAATCGAC GCTCAAGTCA GAGGTGGCGA 3960
AACCCGACAG GACTATAAAG ATACCAGGCG TTTCCCCCTG GAAGCTCCCT CGTGCGCTCT 4020
CCTGTTCCGA CCCTGCCGCT TACCGGATAC CTGTCCGCCT TTCTCCCTTC GGGAAGCGTG 4080
GCGCTTTCTC AATGCTCACG CTGTAGGTAT CTCAGTTCGG TGTAGGTCGT TCGCTCCAAG 4140
CTGGGCTGTG TGCACGAACC CCCCGTTCAG CCCGACCGCT GCGCCTTATC CGGTAACTAT 4200
CGTCTTGAGT CCAACCCGGT AAGACACGAC TTATCGCCAC TGGCAGCAGC CACTGGTAAC 4260
AGGATTAGCA GAGCGAGGTA TGTAGGCGGT GCTACAGAGT TCTTGAAGTG GTGGCCTAAC 4320
TACGGCTACA CTAGAAGGAC AGTATTTGGT ATCTGCGCTC TGCTGAAGCC AGTTACCTTC 4380
GGAAAAAGAG TTGGTAGCTC TTGATCCGGC AAACAAACCA CCGCTGGTAG CGGTGGTTTT 4440
TTTGTTTGCA AGCAGCAGAT TACGCGCAGA AAAAAAGGAT CTCAAGAAGA TCCTTTGATC 4500
TTTTCTACGG GGTCTGACGC TCAGTGGAAC GAAAACTCAC GTTAAGGGAT TTTGGTCATG 4560
AGATTATCAA AAAGGATCTT CACCTAGATC CTTTTAAATT AAAAATGAAG TTTTAAATCA 4620
ATCTAAAGTA TATATGAGTA AACTTGGTCT GACAGTTACC AATGCTTAAT CAGTGAGGCA 4680
CCTATCTCAG CGATCTGTCT ATTTCGTTCA TCCATAGTTG CCTGACTCCC CGTCGTGTAG 4740
ATAACTACGA TACGGGAGGG CTTACCATCT GGCCCCAGTG CTGCAATGAT ACCGCGAGAC 4800
CCACGCTCAC CGGCTCCAGA TTTATCAGCA ATAAACCAGC CAGCCGGAAG GGCCGAGCGC 4860
AGAAGTGGTC CTGCAACTTT ATCCGCCTCC ATCCAGTCTA TTAATTGTTG CCGGGAAGCT 4920
AGAGTAAGTA GTTCGCCAGT TAATAGTTTG CGCAACGTTG TTGCCATTGC TGCAGGCATC 4980
GTGGTGTCAC GCTCGTCGTT TGGTATGGCT TCATTCAGCT CCGGTTCCCA ACGATCAAGG 5040
CGAGTTACAT GATCCCCCAT GTTGTGCAAA AAAGCGGTTA GCTCCTTCGG TCCTCCGATC 5100
GTTGTCAGAA GTAAGTTGGC CGCAGTGTTA TCACTCATGG TTATGGCAGC ACTGCATAAT 5160
TCTCTTACTG TCATGCCATC CGTAAGATGC TTTTCTGTGA CTGGTGAGTA CTCAACCAAG 5220
TCATTCTGAG AATAGTGTAT GCGGCGACCG AGTTGCTCTT GCCCGGCGTC AACACGGGAT 5280
AATACCGCGC CACATAGCAG AACTTTAAAA GTGCTCATCA TTGGAAAACG TTCTTCGGGG 5340
CGAAAACTCT CAAGGATCTT ACCGCTGTTG AGATCCAGTT CGATGTAACC CACTCGTGCA 5400
CCCAACTGAT CTTCAGCATC TTTTACTTTC ACCAGCGTTT CTGGGTGAGC AAAAACAGGA 5460
AGGCAAAATG CCGCAAAAAA GGGAATAAGG GCGACACGGA AATGTTGAAT ACTCATACTC 5520
TTCCTTTTTC AATATTATTG AAGCATTTAT CAGGGTTATT GTCTCATGAG CGGATACATA 5580
TTTGAATGTA TTTAGAAAAA TAAACAAATA GGGGTTCCGC GCACATTTCC CCGAAAAGTG 5640
CCACCTGACG TCTAAGAAAC CATTATTATC ATGACATTAA CCTATAAAAA TAGGCGTATC 5700
ACGAGGCCCT TTCGTCTTCA AGAATTCATA CCAGATCACC GAAAACTGTC CTCCAAATGT 5760
GTCCCCCTCA CACTCCCAAA TTCGCGGGCT TCTGCCTCTT AGACCACTCT ACCCTATTCC 5820
CCACACTCAC CGGAGCCAAA GCCGCGGCCC TTCCGTTTCT TGCT 5865
```

*FIG. 2B-2.*

| Sample | OD of reaction product measured at 490 nm |
|---|---|
| 1. PLP peptide 139-151 | 1.06∓0.41 |
| 2. HIV gp120 peptide control | 0.10∓0.09 |
| 3. Supernatant of SJL fibroblasts transduced with PLP retrovirus. Sample I | 0.92∓0.50 |
| 4. Supernatant of SJL cultured fibroblasts transduced with PLP retrovirus. Sample II | 0.73∓0.17 |
| 5. Supernatant of cultured fibroblasts transduced with β-galactosidase (LacZ) construct | 0.05∓0.01 |

1. PLP and HIV gp120 peptides used at a concentration of 5 ug/ml.
2. All supernatants used undiluted.
3. Primary monoclonal antibody was used as an undiluted hybridoma supernatant.
4. Peroxidase conjugated secondary goat anti-antibody used at a dilution 1:500.

FIG. 5.

| Grade 0 | no abnormality |
| --- | --- |
| Grade 1 | slow, sluggish |
| Grade 2 | limp tail |
| Grade 3 | limp tail, hand/limb weakness, waddling gait |
| Grade 4 | partial hind limb paralysis |
| Grade 5 | complete hind limb paralysis |
| Grade 6 | animal immobile |
| Grade 7 | moribund |

FIG. 7.

1+  mild (1-3 small foci)

2+  moderate (more than 3-7 foci containing at least 10)

3+  severe (large foci of 15 to 25 cells with perivascular and meningeal collections)

4+  severe with necrosis and demyelination

| # Grade Animals | Day 55-60 | | | | | Day 90-95 | | | | |
|---|---|---|---|---|---|---|---|---|---|---|
| | A 40 | B 28 | C 38 | D 30 | E 32 | A 17 | B 13 | C 8 | D 14 | E 18 |
| 0 | 2 | 2 | 0 | 1 | 30 | 0 | 2 | 0 | 0 | 17 |
| 1 | 2 | 0 | 0 | 1 | 1 | 1 | 0 | 4 | 1 | 0 |
| 2 | 14 | 10 | 20 | 8 | 0 | 0 | 0 | 4 | 8 | 0 |
| 3 | 14 | 11 | 11 | 3 | 0 | 10 | 11 | 0 | 4 | 0 |
| 4 | 5 | 1 | 2 | 2 | 1* | 4 | 0 | 0 | 1 | 1* |
| 5 | 0 | 0 | 1 | 2 | 0 | 0 | 0 | 0 | 0 | 0 |
| 6 | 3 | 4 | 4 | 0 | 0 | 3 | 0 | 0 | 0 | 0 |
| 7 | 0 | 0 | 0 | 0 | 0 | 0 | 0 | 0 | 0 | 0 |

\* Paralysis with first relapse no further progression.

A = EAE control; B = EAE + untransduced fibroblasts; C = EAE + fibroblasts with Lac-Z retrovirus; D = EAE + neo fibroblasts with neo-retrovirus; E = EAE + PLP fibroblasts with PLP-retrovirus.

|  | Day 55-60 | | | | | | Day 90-95 | | | | | |
| --- | --- | --- | --- | --- | --- | --- | --- | --- | --- | --- | --- | --- |
|  | 0 | + | ++ | +++ | ++++ | | 0 | + | ++ | +++ | ++++ | |
| EAE Control | 1 | 2 | 2 | 1 | 2 | | 0 | 0 | 0 | 3 | 5 | |
| EAE Untransduced fibroblasts | 0 | 3 | 0 | 2 | 3 | | 1 | 2 | 1 | 2 | 2 | |
| EAE Neoretrovirus | 2 | 2 | 0 | 3 | 1 | | 0 | 1 | 3 | 2 | 1 | |
| EAE LacZ-retrovirus | 2 | 1 | 1 | 1 | 3 | | 0 | 0 | 4 | 1 | 2 | |
| EAE PLP-retrovirus | 7 | 0 | 1 | 0 | 0 | | 5 | 1 | 1 | 0 | 1* | |

* paralyzed animal

FIG. 10A.

Pathologic Assessment of Brain and Spinal Cords from Days 55-60 through Days 90-95

| TREATMENT DAY 21 | Score 2+ or more |
|---|---|
| EAE Control | 13/16 |
| Untransduced fibroblasts | 10/16 |
| Neo-retrovirus | 10/15 |
| LacZ-retrovirus | 12/15 |
| PLP-retrovirus | 3/16 |

FIG. 10B.

| Mouse | 0 | + | Score ++ | +++ | ++++ | Total (Score 2+ or more) |
|---|---|---|---|---|---|---|
| EAE Control | 0 | 1 | 2 | 0 | 1 | 3/4 |
| Untranduced fibroblasts | 0 | 3 | 6 | 4 | 1 | 11/14 |
| Neo-retrovirus | 0 | 5 | 3 | 4 | 0 | 7/12 |
| LacZ-retrovirus | 0 | 2 | 7 | 3 | 0 | 10/12 |
| PLP-retrovirus | 11 | 3 | 0 | 0 | 0 | 0/14 |

FIG. 11.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:1:

```
GATGGTGACC GGAGATCTGC CGCCACCATG GGGGCGATGG CTCCGCGCAC GCTGCTCCTG      60

CTGCTGGCGG CCGCCCTGGC CCCGACTCAG ACCCGCGCGG GGCCCGGCGA CTACAAGACC     120

ACCATCTGCG GCAAGGGCCT GAGCGCAACG GTAACAGGGG GCCAGAAGGG GAGGGGTTCC     180

AGAGGCCAAC ATCAAGCTCA TTCTCTCGAG CGGGTGTGTC ATTGTTTGGG AAAATGGCTA     240

GGACATCCCG ACAAGTTTGT GGGCATCACC TATGCTAGCC TTAAGTAGGA TCCTTGAATA     300

GGTAAGCTTG CTAGCCC                                                    317
```

(2) INFORMATION FOR SEQ ID NO:2:

(i) SEQUENCE CHARACTERISTICS:
        (A) LENGTH: 5865 base pairs
        (B) TYPE: nucleic acid
        (C) STRANDEDNESS: double
        (D) TOPOLOGY: circular (ii) MOLECULE TYPE: Genomic DNA (xi) SEQUENCE DESCRIPTION: SEQ ID NO:2:

```
TTTGAAAGAC CCCACCCGTA GGTGGCAAGC TAGCTTAAGT AACGCCACTT TGCAAGGCAT      60
GGAAAAATAC ATAACTGAGA ATAGAAAAGT TCAGATCAAG GTCAGGAACA AAGAAACAGC     120
TGAATACCAA ACAGGATATC TGTGGTAAGC GGTTCCTGCC CCGGCTCAGG GCCAAGAACA     180
GATGAGACAG CTGAGTGATG GGCCAAACAG GATATCTGTG GTAAGCAGTT CCTGCCCCGG     240
CTCGGGGCCA AGAACAGATG GTCCCCAGAT GCGGTCCAGC CCTCAGCAGT TTCTAGTGAA     300
TCATCAGATG TTTCCAGGGT GCCCCAAGGA CCTGAAAATG ACCCTGTACC TTATTTGAAC     360
TAACCAATCA GTTCGCTTCT CGCTTCTGTT CGCGCGCTTC CGCTCTCCGA GCTCAATAAA     420
AGAGCCCACA ACCCCTCACT CGGCGCGCCA GTCTTCCGAT AGACTGCGTC GCCCGGGTAC     480
CCGTATTCCC AATAAAGCCT CTTGCTGTTT GCATCCGAAT CGTGGTCTCG CTGTTCCTTG     540
GGAGGGTCTC CTCTGAGTGA TTGACTACCC ACGACGGGGG TCTTTCATTT GGGGGCTCGT     600
CCGGGATTTG GAGACCCCTG CCCAGGGACC ACCGACCCAC CACCGGGAGG TAAGCTGGCC     660
AGCAACTTAT CTGTGTCTGT CCGATTGTCT AGTGTCTATG TTTGATGTTA TGCGCCTGCG     720
TCTGTACTAG TTAGCTAACT AGCTCTGTAT CTGGCGGACC CGTGGTGGAA CTGACGAGTT     780
CTGAACACCC GGCCGCAACC CTGGGAGACG TCCCAGGGAC TTTGGGGGCC GTTTTTGTGG     840
CCCGACCTGA GGAAGGGAGT CGATGTGGAA TCCGACCCCG TCAGGATATG TGGTTCTGGT     900
AGGAGACGAG AACCTAAAAC AGTTCCCGCC TCCGTCTGAA TTTTTGCTTT CGGTTTGGAA     960
CCGAAGCCGC GCGTCTTGTC TGCTGCAGCG CTGCAGCATC GTTCTGTGTT GTCTCTGTCT    1020
GACTGTGTTT CTGTATTTGT CTGAAAATTA GGGCCAGACT GTTACCACTC CCTTAAGTTT    1080
GACCTTAGGT CACTGGAAAG ATGTCGAGCG GATCGCTCAC AACCAGTCGG TAGATGTCAA    1140
GAAGAGACGT TGGGTTACCT TCTGCTCTGC AGAATGGCCA ACCTTTAACG TCGGATGGCC    1200
GCGAGACGGC ACCTTTAACC GAGACCTCAT CACCCAGGTT AAGATCAAGG TCTTTTCACC    1260
TGGCCCGCAT GGACACCCAG ACCAGGTCCC CTACATCGTG ACCTGGGAAG CCTTGGCTTT    1320
TGACCCCCCT CCCTGGGTCA AGCCCTTTGT ACACCCTAAG CCTCCGCCTC CTCTTCCTCC    1380
ATCCGCCCCG TCTCTCCCCC TTGAACCTCC TCGTTCGACC CCGCCTCGAT CCTCCCTTTA    1440
TCCAGCCCTC ACTCCTTCTC TAGGCGCCGG AATTCGCGGC CGCTACGTAG TCGACTCGCT    1500
GTGGAATGTG TGTCAGTTAG GGTGTGGAAA GTCCCCAGGC TCCCCAGCAG GCAGAAGTAT    1560
GCAAAGCATG CATCTCAATT AGTCAGCAAC CAGGTGTGGA AAGTCCCCAG GCTCCCCAGC    1620
AGGCAGAAGT ATGCAAAGCA TGCATCTCAA TTAGTCAGCA ACCATAGTCC CGCCCCTAAC    1680
TCCGCCCATC CCGCCCCTAA CTCCGCCCAG TTCCGCCCAT TCTCCGCCCC ATGGCTGACT    1740
AATTTTTTTT ATTTATGCAG AGGCCGAGGC CGCCTCGGCC TCTGAGCTAT TCCAGAAGTA    1800
GTGAGGAGGC TTTTTTGGAG GCCTAGGCTT TTGCAAAAAG CTCGAAGATC AATTCCGATC    1860
TGATCAAGAG ACAGGATGAG GATCGTTTCG CATGATTGAA CAAGATGGAT TGCACGCAGG    1920
TTCTCCGGCC GCTTGGGTGG AGAGGCTATT CGGCTATGAC TGGGCACAAC AGACAATCGG    1980
CTGCTCTGAT GCCGCCGTGT TCCGGCTGTC AGCGCAGGGG CGCCCGGTTC TTTTTGTCAA    2040
GACCGACCTG TCCGGTGCCC TGAATGAACT GCAGGACGAG GCAGCGCGGC TATCGTGGCT    2100
GGCCACGACG GGCGTTCCTT GCGCAGCTGT GCTCGACGTT GTCACTGAAG CGGGAAGGGA    2160
CTGGCTGCTA TTGGGCGAAG TGCCGGGGCA GGATCTCCTG TCATCTCACC TTGCTCCTGC    2220
```

```
CGAGAAAGTA TCCATCATGG CTGATGCAAT GCGGCGGCTG CATACGCTTG ATCCGGCTAC    2280

CTGCCCATTC GACCACCAAG CGAAACATCG CATCGAGCGA GCACGTACTC GGATGGAAGC    2340

CGGTCTTGTC GATCAGGATG ATCTGGACGA AGAGCATCAG GGGCTCGCGC AGCCGAACT     2400

GTTCGCCAGG CTCAAGGCGC GCATGCCCGA CGGCGAGGAT CTCGTCGTGA CCCATGGCGA    2460

TGCCTGCTTG CCGAATATCA TGGTGGAAAA TGGCCGCTTT TCTGGATTCA TCGACTGTGG    2520

CCGGCTGGGT GTGGCGGACC GCTATCAGGA CATAGCGTTG GCTACCCGTG ATATTGCTGA    2580

AGAGCTTGGC GGCGAATGGG CTGACCGCTT CCTCGTGCTT TACGGTATCG CCGCTCCCGA    2640

TTCGCAGCGC ATCGCCTTCT ATCGCCTTCT TGACGAGTTC TTCTGAGCGG GACTCTGGGG    2700

TTCGTCGAGA AGCTTGGGCC CATCGATAAA ATAAAAGATT TTATTTAGTC TCCAGAAAAA    2760

GGGGGGAATG AAAGACCCCA CCTGTAGGTT TGGCAAGCTA GCTTAAGTAA CGCCATTTTG    2820

CAAGGCATGG AAAATACAT AACTGAGAAT AGAGAAGTTC AGATCAAGGT CAGGAACAGA     2880

TGGAACAGCT GAATATGGGC CAAACAGGAT ATCTGTGGTA AGCAGTTCCT GCCCCGGCTC    2940

AGGGCCAAGA ACAGATGGAA CAGCTGAATA TGGGCCAAAC AGGATATCTG TGGTAAGCAG    3000

TTCCTGCCCC GGCTCAGGGC CAAGAACAGA TGGTCCCCAG ATGCGGTCCA GCCCTCAGCA    3060

GTTTCTAGAG AACCATCAGA TGTTTCCAGG GTGCCCCAAG GACCTGAAAT GACCCTGTGC    3120

CTTATTTGAA CTAACCAATC AGTTCGCTTC TCGCTTCTGT TCGCGCGCTT CTGCTCCCCG    3180

AGCTCAATAA AAGAGCCCAC AACCCCTCAC TCGGGCGCC AGTCCTCCGA TTGACTGAGT     3240

CGCCCGGGTA CCCGTGTATC AATAAACCC TCTTGCAGTT GCATCCGACT TGTGGTCTCG     3300

CTGTTCCTTG GGAGGGTCTC CTCTGAGTGA TTGACTACCC GTCAGCGGGG GTCTTTCATT    3360

TGGGGGCTCG TCCGGGATCG GGAGACCCCT GCCCAGGGAC CACCGACCCA CCACCGGGAG    3420

GTAAGCTGGC TGCCTCGCGC GTTTCGGTGA TGACGGTGAA AACCTCTGAC ACATGCAGCT    3480

CCCGGAGACG GTCACAGCTT GTCTGTAAGC GGATGCCGGG AGCAGACAAG CCCGTCAGGG    3540

CGCGTCAGCG GGTGTTGGCG GGTGTCGGG CGCAGCCATG ACCCAGTCAC GTAGCGATAG     3600

CGGAGTGTAT ACTGGCTTAA CTATGCGGCA TCAGAGCAGA TTGTACTGAG AGTGCACCAT    3660

ATGCGGTGTG AAATACCGCA CAGATGCGTA AGGAGAAAAT ACCGCATCAG GCGCTCTTCC    3720

GCTTCCTCGC TCACTGACTC GCTGCGCTCG GTCGTTCGGC TGCGGCGAGC GGTATCAGCT    3780

CACTCAAAGG CGGTAATACG GTTATCCACA GAATCAGGGG ATAACGCAGG AAAGAACATG    3840

TGAGCAAAAG GCCAGCAAAA GGCCAGGAAC CGTAAAAAGG CCGCGTTGCT GGCGTTTTTC    3900

CATAGGCTCC GCCCCCCTGA CGAGCATCAC AAAAATCGAC GCTCAAGTCA GAGGTGGCGA    3960

AACCCGACAG GACTATAAAG ATACCAGGCG TTTCCCCCTG GAAGCTCCCT CGTGCGCTCT    4020

CCTGTTCCGA CCCTGCCGCT TACCGGATAC CTGTCCGCCT TTCTCCCTTC GGGAAGCGTG    4080

GCGCTTTCTC AATGCTCACG CTGTAGGTAT CTCAGTTCGG TGTAGGTCGT TCGCTCCAAG    4140

CTGGGCTGTG TGCACGAACC CCCCGTTCAG CCCGACCGCT GCGCCTTATC CGGTAACTAT    4200

CGTCTTGAGT CCAACCCGGT AAGACACGAC TTATCGCCAC TGGCAGCAGC CACTGGTAAC    4260

AGGATTAGCA GAGCGAGGTA TGTAGGCGGT GCTACAGAGT TCTTGAAGTG GTGGCCTAAC    4320

TACGGCTACA CTAGAAGGAC AGTATTTGGT ATCTGCGCTC TGCTGAAGCC AGTTACCTTC    4380

GGAAAAAGAG TTGGTAGCTC TTGATCCGGC AAACAAACCA CCGCTGGTAG CGGTGGTTTT    4440

TTTGTTTGCA AGCAGCAGAT TACGCGCAGA AAAAAGGAT CTCAAGAAGA TCCTTTGATC     4500

TTTTCTACGG GGTCTGACGC TCAGTGGAAC GAAAACTCAC GTTAAGGGAT TTTGGTCATG    4560

AGATTATCAA AAAGGATCTT CACCTAGATC CTTTTAAATT AAAAATGAAG TTTTAAATCA    4620
```

-continued

```
ATCTAAAGTA TATATGAGTA AACTTGGTCT GACAGTTACC AATGCTTAAT CAGTGAGGCA    4680

CCTATCTCAG CGATCTGTCT ATTTCGTTCA TCCATAGTTG CCTGACTCCC CGTCGTGTAG    4740

ATAACTACGA TACGGGAGGG CTTACCATCT GGCCCCAGTG CTGCAATGAT ACCGCGAGAC    4800

CCACGCTCAC CGGCTCCAGA TTTATCAGCA ATAAACCAGC CAGCCGGAAG GGCCGAGCGC    4860

AGAAGTGGTC CTGCAACTTT ATCCGCCTCC ATCCAGTCTA TTAATTGTTG CCGGGAAGCT    4920

AGAGTAAGTA GTTCGCCAGT TAATAGTTTG CGCAACGTTG TTGCCATTGC TGCAGGCATC    4980

GTGGTGTCAC GCTCGTCGTT TGGTATGGCT TCATTCAGCT CCGGTTCCCA ACGATCAAGG    5040

CGAGTTACAT GATCCCCCAT GTTGTGCAAA AAAGCGGTTA GCTCCTTCGG TCCTCCGATC    5100

GTTGTCAGAA GTAAGTTGGC CGCAGTGTTA TCACTCATGG TTATGGCAGC ACTGCATAAT    5160

TCTCTTACTG TCATGCCATC CGTAAGATGC TTTTCTGTGA CTGGTGAGTA CTCAACCAAG    5220

TCATTCTGAG AATAGTGTAT GCGGCGACCG AGTTGCTCTT GCCCGGCGTC AACACGGGAT    5280

AATACCGCGC CACATAGCAG AACTTTAAAA GTGCTCATCA TTGGAAAACG TTCTTCGGGG    5340

CGAAAACTCT CAAGGATCTT ACCGCTGTTG AGATCCAGTT CGATGTAACC CACTCGTGCA    5400

CCCAACTGAT CTTCAGCATC TTTTACTTTC ACCAGCGTTT CTGGGTGAGC AAAAACAGGA    5460

AGGCAAAATG CCGCAAAAAA GGGAATAAGG GCGACACGGA AATGTTGAAT ACTCATACTC    5520

TTCCTTTTTC AATATTATTG AAGCATTTAT CAGGGTTATT GTCTCATGAG CGGATACATA    5580

TTTGAATGTA TTTAGAAAAA TAAACAAATA GGGGTTCCGC GCACATTTCC CCGAAAAGTG    5640

CCACCTGACG TCTAAGAAAC CATTATTATC ATGACATTAA CCTATAAAAA TAGGCGTATC    5700

ACGAGGCCCT TTCGTCTTCA AGAATTCATA CCAGATCACC GAAAACTGTC CTCCAAATGT    5760

GTCCCCCTCA CACTCCCAAA TTCGCGGGCT TCTGCCTCTT AGACCACTCT ACCCTATTCC    5820

CCACACTCAC CGGAGCCAAA GCCGCGGCCC TTCCGTTTCT TTGCT                    5865
```

CONSTRUCTION AND USE OF GENES ENCODING PATHOGENIC EPITOPES FOR TREATMENT OF AUTOIMMUNE DISEASE

FIELD OF THE INVENTION

This invention relates generally to the field of immunotherapy and to the preparation and use of engineered cells having the ability to restore tolerance to self antigens in patients suffering from autoimmune disease. More particularly, this invention relates to the design and construction of a gene encoding an encephalogenic epitope of proteolipid protein (PLP), to methods of in vitro and in vivo expression of a PLP epitope, to methods of in vivo secretion of a PLP epitope, and to methods of transferring the partial PLP gene to a host to ameliorate the progression of an immune response to self antigens derived from myelin proteins.

BACKGROUND OF THE INVENTION

The immune system can respond in two ways when exposed to an antigen. A positive response leads to differentiation of T and B cells, antibody production and to immunologic memory. A negative response leads to suppression or inactivation of specific lymphocytes and to tolerance. Tolerance can be defined as the failure of an organism to mount an immune response against a specific antigen. Normally, an organism is tolerant of its own antigens.

Autoimmune diseases are thought to result from an uncontrolled immune response directed against self antigens. In patients with multiple sclerosis (MS), for example, there is evidence that this attack is against the white matter of the central nervous system and more particularly to white matter proteins. Ultimately, the myelin sheath surrounding the axons is destroyed. This can result in paralysis, sensory deficits and visual problems. MS is characterized by a T cell and macrophage infiltrate in the brain. Autoreactive myelin-specific T cells have been isolated from MS patients, although T cells of the same specificity have been detected in normal individuals. J. M. LaSalle et al., *J. Immunol.* 147:774–780 (1991), J. M. LaSalle et al., *J. Exp. Med.* 176:177–186 (1992), J. Correale et al., *Neurology*. 45:1370–1378 (1995). Presently, the myelin proteins thought to be the target of an immune response in MS include myelin basic protein (MBP), proteolipid protein (PLP), and myelin-oligodendrocyte glycoprotein (MOG). Individuals who do not mount an autoimmune response to self proteins are thought to have control over these responses and are believed to be "tolerant" of self antigens. The evidence, therefore, that MS is caused by pathogenic T cells is necessarily indirect, but the close resemblance which the characteristics of this disease bear to those of the murine model, experimental autoimmune encephalomyelitis (EAE), suggest that MS is indeed caused by an aberrant immune response mediated by T cells.

The EAE mouse model for MS, the subject of intense and fruitful study for several years, displays many of the same histopathological and clinical characteristics as the relapsing remitting forms of MS. The T Lymphocyte in Experimental Allergic Encephalomyelitis, Ann. Rev. Immunol. 8:579–621 (1990). EAE can be induced in SJL mice by injection of mouse spinal cord homogenate (MSCH), MBP, PLP, by the injection of synthetic peptides whose sequences correspond to the major encephalogenic epitopes of myelin basic protein, MBP 84–104, proteolipid protein, PLP 139–151, or by adoptive transfer of activated CD4$^+$ $T_{H1}$, but not $T_{H2}$ cells specific for encephalogenic epitopes. The major encephalogenic epitopes of myelin-derived sequences in EAE, such as MBP, can also activate human T cells of several different haplotypes including HLA-DR2. R. Martin, et al., *J. Exp. Med.* 173:19–24 (1992). The experimental disease is characterized by a relapsing-remitting course (R-EAE) of neurological dysfunction, perivascular mononuclear infiltration and demyelination. CNS damage is probably mediated by inflammatory cytokines which can activate additional monocytes and macrophages non-specifically. J. E. Blalock, The Immune System. Our Sixth Sense, The Immunologist, 2:8–15 (1994).

Although the initial attack in EAE can be induced by the administration of either T cells specific for MBP or for PLP, close examination of reactivities of T cells in the primary and subsequent relapses demonstrates the presence of T cells which interact with specificities other than the inducing epitopes. This expansion of encephalogenic epitopes is termed "determinant spreading". S. D. Miller and W. J. Karpus, *Immunology Today* 15:356–361 (1994), P. V. Lehman, T. Forsthuber, A. Miller, and E. E. Sercarz, *Nature* 358–155–157 (1992), H. Jiang, S-I. Zhang and B. Pernis, *Science* 256:1213–1215 (1992). Antigen specific treatment would therefore, be expected to be more effective when administered early in the course of the disease, before the onset of increasing epitope complexity and eventual non-specific inflammation.

The goal of immunologic therapy is to restore tolerance without suppressing the entire immune system which can lead to complications such as infection, hemorrhage, and cancer. Drugs currently used to treat autoimmune diseases are non-specific immunosuppressive agents, such as anti-inflammatory agents or drugs which can block cell proliferation or depress proinflammatory cytokines. In general, these agents are effective for limited duration and subject to devastating complications.

It is desirable to suppress the immune system in a more specific way to control the response to self-antigens and theoretically "cure" the disease without down-regulating the entire immune system. Several specific immunotherapies have been hypothesized and tested in recent years, many of which are impractical or do not work in humans. For example, high affinity peptides can be synthesized which interact with MHC class II molecules and prevent the binding of encephalogenic peptides, thereby preventing the activation of pathogenic T cells. A. Franco et al., *The Immunologist* 2:97–102 (1994). This approach is disadvantageous in that it is difficult to obtain effective concentrations of inhibitor peptides in vivo. G. Y. Ishioka et al., *J. Immunol.* 152:4310–4319. In an alternate strategy, peptides which are analogs of encephalogenic sequences have been shown to antagonize the T cell receptors of antigen-specific T cells, rendering them unreactive, although the exact mechanism is at present unknown. S. C. Jameson et al., *J. Exp. Med* 177:1541–1550 (1993), N. Karin et al., *J. Exp. Med.* 180:2227–2237 (1994), V. K. Kuchroo et al., *J. Immunol.* 153:3326–3336 (1994). Oral administration of myelin has been tested and found to induce a state of immunological unresponsiveness thought to be mediated by the induction of suppressor T cell or of anergy. H. L. Weiner et al., *Annu. Rev. Immunol.* 12:809–837 (1994), C. C. Whitacre et al., *J. Immunol.* 147:2155–2163 (1991), S. J. Khoury et al., *J. Exp. Med.* 176:1355–1364 (1992). This treatment has been found to be efficacious for some but not all individuals. H. L. Weiner et al., *Science* 259:1321–1324 (1993). Thus, it is evident that improvements are needed to treat MS and other autoimmune disorders with an effective, immunospecific approach.

SUMMARY OF THE INVENTION

The present invention addresses the disadvantages present in the prior art. In general, the invention is based on the discovery that recombinant DNA technology and cell transfer may be employed to restore tolerance to one's own tissues. The present invention provides a means of preparing and constructing a gene, that when expressed and secreted in vivo, can provide a means of halting the progression of an autoimmune disease. In further aspects the invention provides a method to construct a gene encoding a portion of a CNS protein, insert the gene sequence into a vector and transfect a cell line. In further aspects, the invention provides a method to construct a gene encoding a portion of a CNS protein, insert the sequence into a retroviral vector, and transduce a producer fibroblast cell line to generate supernatant containing the recombinant retrovirus. Histocompatible fibroblasts are transduced with the recombinant retrovirus encoding a portion of the CNS protein and are delivered to animals. These fibroblasts continuously secrete a CNS antigen in vivo but do not themselves produce viral particles.

In accordance with the present invention, we have used synthetic oligonucleotides to construct a gene encoding a portion of the PLP protein, performed expression of the DNA in combination with various expression vectors, and thereby evaluated expression levels of the gene product in vitro and in vivo. After transduced histocompatible fibroblasts that secrete the partial PLP protein are transplanted into EAE mice, the disease disappears. The effect is the amelioration of both clinical symptoms and signs and pathological findings.

In a preferred embodiment of the invention, the producer line PA317 is transduced with the PLP retroviral vector to generate supernatant containing the recombinant retrovirus. The producer cell line PA317 was developed by Dr. A. Dusty Miller and has been extensively characterized and approved for human use by the FDA for other clinical trials, such as for genetic diseases and cancer. Miller and Baltimore, *Mol. Cell Biol.* 6:2895–2902 (1986), W. F. Anderson, *Science* 256:808–813.

BRIEF DESCRIPTION OF THE DRAWINGS

FIG. 5 demonstrates the level of PLP protein in the supernatants of transduced fibroblasts as detected by ELISA.

FIG. 7 illustrates the clinical scoring system for chronic EAE.

FIG. 8 illustrates the histological scoring system for EAE.

FIG. 9 illustrates the clinical assessment of EAE mice treated with retrovirus transduced fibroblasts.

FIGS. 10(A+B) 10*a* shows the pathologic assessment of brain and spinal cord of SJL mice treated with retrovirus transduced fibroblasts, and 10*b* is a summary of the pathologic assessment of brain and spinal cord from Days 55–60 through days 90–95.

FIG. 11 shows the histology of SJL mice with chronic EAE treated with retrovirus transduced fibroblasts.

DETAILED DESCRIPTION OF THE INVENTION

Figure 1:
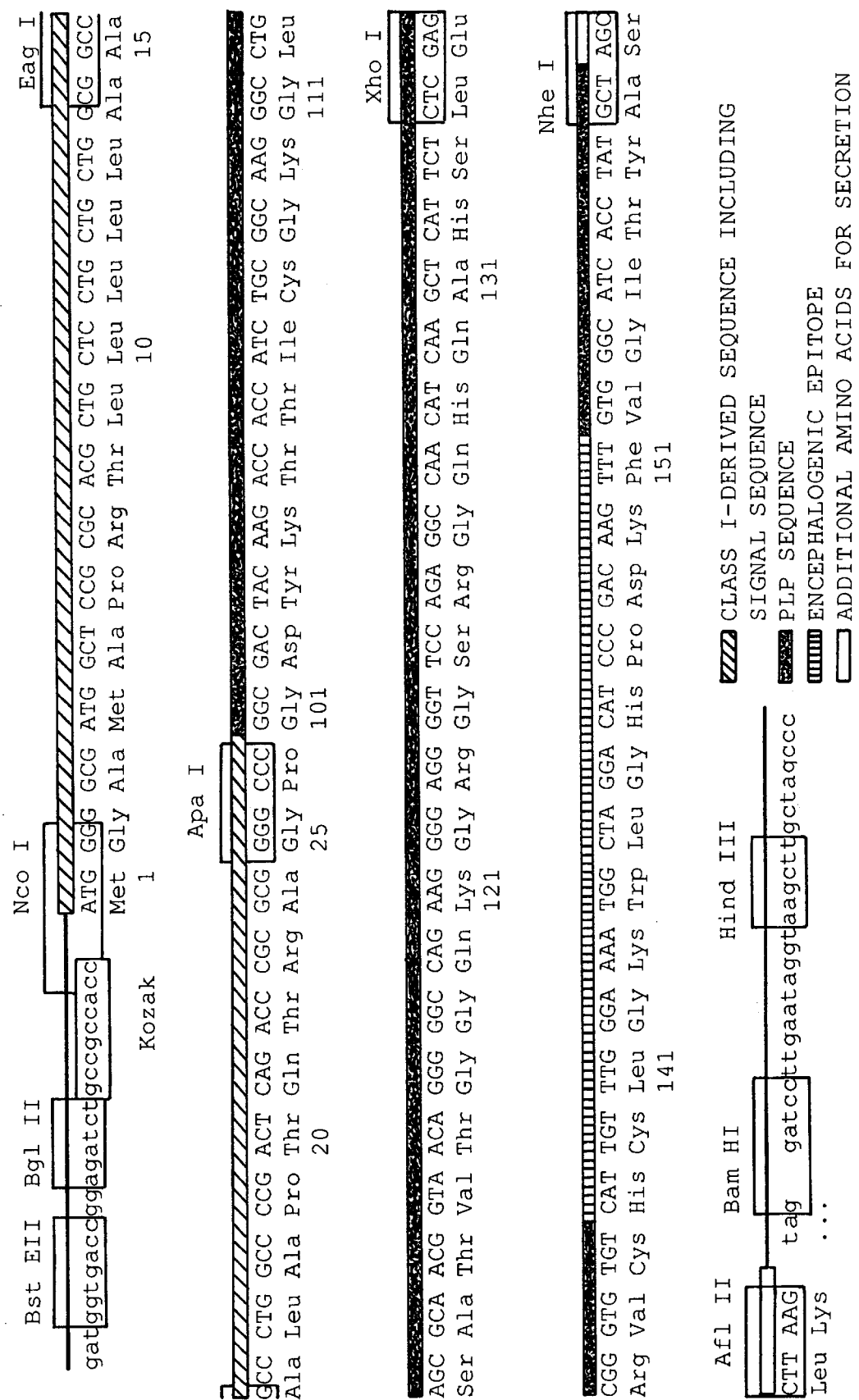
FIG. 1 is a map of the partial PLP gene showing the sequence of the gene product and restriction sites.

As indicated above, the present invention relates to the use of engineered cells to restore tolerance to self antigens in patients suffering from autoimmune disease. The engineered cells can be any mammalian cell. As used herein, the term "engineered" is intended to refer to a cell into which one or more recombinant genes, such as a gene encoding an epitope of a self antigen, has been introduced.

A gene is a deoxyribonucleotide sequence coding for an amino acid sequence. Recombinantly introduced genes will either be in the form of a synthetic oligonucleotide, a cDNA gene (i.e. they will not contain introns), a copy of a genomic gene sequence, or a hybrid gene which is a fusion of two or more gene sequences. Optionally the gene may be linked to one or more nucleotide sequence capable of directing expression of the gene product. Sequence elements capable of effecting expression of a gene or gene product include but are not limited to promoters, enhancer elements, transcription termination signals, polyadenylation sites, a Kozak box sequence to ensure efficient translation, and leader sequences. Optionally, the gene sequence can include restriction sites to enable the insertion of additional gene sequences. Preferably, the gene will contain a leader sequence to ensure the gene product is synthesized in the endoplasmic reticulum for later constitutive secretion.

Recombinantly introduced genes carried by the engineered cells can encode one or more epitope, fragment, domain or mini-protein portion of a protein antigen. Examples of suitable proteins from which an epitope, fragment, domain, or mini-protein may be derived include but are not limited to myelin proteins, acetylcholine receptor, TSH receptor, and collagen.

It is believed that protein self-antigens which are the target of an autoimmune response are highly conserved both among and between species. Thus, although the invention will primarily be used to treat humans it can also be used to treat animals. Examples of T cell mediated autoimmune diseases that may be treated using the invention include but are not limited to multiple sclerosis, myasthenia gravis, systemic lupus erythematosus, psoriasis, juvenile onset diabetes, rheumatoid arthritis, thyroid disease and chronic inflammatory demyelinating polyneuropathy (CIDP).

Expression vectors are generally deoxyribonucleotide molecules engineered for controlled expression of one or more desired genes. The vectors may comprise one or more nucleotide sequences operably linked to a gene to control expression of the desired gene or genes. There are an abundance of expression vectors available and one skilled in the art could easily select an appropriate vector. In addition, standard laboratory manuals on genetic engineering provide recombinant DNA methods and methods for making and using expression vectors. Optionally, the vector may encode a selectable marker, for example, antibiotic resistance.

The gene can be inserted into the mammalian cell using any gene transfer procedure. Examples of such procedures include but are not limited to, RNA viral mediated gene transfer such as retroviral transduction, DNA viral mediated gene transfer, electroporation, calcium phosphate mediated transfection, microinjection or liposome mediated gene transfer. The type of procedure required to achieve an engineered cell that secretes the desired gene product will depend on the nature and properties of the cell. The specific technology for introducing such genes into such cells is generally known and well within the skill of the art.

The examples which follow illustrate the design and construction of a portion of the PLP gene, in vitro and in vivo expression of the PLP gene product, and the in vivo effects of the PLP gene product.

The following examples are presented to illustrate the invention, and are not intended to limit the scope thereof.

EXAMPLE 1

DESIGN AND CONSTRUCTION OF THE PLP GENE

In SJL/J mice, the encephalogenic epitope of PLP comprises amino acids 139–151. N Takahashi et al., *Cell* 42:139–148 (1985), K Sakai et al., *J. Neuroimmunol.* 19:21–32 (1988), D. H. Kono et al., *J. Exp. Med.* 168:213–227. The vector in the present invention is designed in order that the gene product encoded by it be constitutively secreted from fibroblasts. Since the complete PLP protein is a hydrophobic transmembrane protein (H-J. Diehl, M. Schaich, R-M. Buszinski and W. Stoffel, *PNAS U.S.A.* 83:9807–9811 (1986)), with the encephalogenic epitope being extracellular, a plasmid encoding amino acids 101–157 and additional amino acids required for secretion was constructed. This sequence is hydrophilic in character.
1. Oligonucleotide Synthesis and Construction of the PLP pRc/CMV Vector Oligonucleotides can be synthesized manually, e.g., by the phospho-tri-ester method, as disclosed, for example in R. L. Letsinger, et. al., *J. Am. chem. Soc.* 98:3655 (1967), the disclosure of which is incorporated by reference. Other methods are well known in the art. See also Matteucci and Caruthers, *J. Am. Chem. Soc.* 103:3185 (1981), the disclosure of which is incorporated by reference.

Preferably, however, the desired gene sequence can be made by automated synthesis of individual oligonucleotides at 0.2 μM concentrations. For PLP amino acids 101–157, DNA syntheses were performed on a Perkin Elmer/Applied Biosystems Division Model 394 DNA synthesizer using cyanoethyl-protected phosphoramidites. The dimethoxytrityl (DMT) group was not removed from the 5'hydroxyl group to allow for purification. After normal cleavage from the resin using concentrated ammonium hydroxide and deprotection at 55° C. for 16 hours, the oligonucleotides were purified using oligonucleotide purification cartridges (OPC) according to the manufacturer's instructions (Applied Biosystems Inc.) Five oligonucleotides of the following sequences were synthesized:
OLG1
5'-CGGCGACTACAAGACCACCATCTGCGGCAA GGGCCTGAGCGCAACGGTAACAG GGGGCCA- GAAGGGGAGGGGTTCCAGAGGCCAACAT- CAAGCTCATTCTCTCGA GC-3',
OLG2
5'-GAGCTTGATGTTGGCCTCTGGAACCCCTCCCC TTCTGGCCCCCTGTTACCGTT GCGCTCAGGC- CCTTGCCGCAGATGGTGGTCTTG TAGTCGCCGGGCC-3',
OLG3
5'-GGGTGTGTCATTGTTTGGGAAAATGGCTAGGA CATCCCGACAAGTTTGTGGGC ATCACCTAT- GCTAGCCTTAAGTAGGATCCTTG AATAGGTA-3',
OLG4 5'-AGCTTACCTATTCAAGGATCCTACTTAAGG CTAGCATAGGTGATGCCCA-3', and
OLG5
5'-CAAACTTGTCGGGATGTCCTAGCCATTTTCCC AAACAATGACACACCCGCTCG AGAGAAT-3'.

Each purified oligonucleotide was dried under vacuum, washed with 1 ml of sterile double distilled water and then concentrated to dryness under vacuum (Speed vac evaporator; Savant Inc.). 80 pM of each oligomer was kinased at 37° C. for 1 hour by resuspending in 56.6 μl of 1× kinase buffer (Polynucleotide Kinase Buffer; Boehringer Mannheim, Indianapolis, Ind.) containing 10 units of polynucleotide kinase (Boehringer Mannheim) and 100 μM of ATP. The individual oligonucleotides were combined in the presence of 2× SSC (0.03M Sodium Citrate, pH 7.0, and 0.3M NaCl) in a PCR tube with their respective complementary oligomer partners for annealing. Each annealed set measured 200 μl in volume. Oligomer OLG1 was annealed with OLG2, and oligomers OLG4 and OLG5 were annealed with OLG3. Annealing was performed in a Perkin-Elmer 9600 Thermocycler, programmed as follows: 1)99.9° for 2 minutes, and 2) 99.9° to 4° in 15 minutes. During the temperature descent to 4° C., when the thermocycler temperature reached 37° C., the solution containing the oligomer duplex OLG1 and OLG2 was combined with the solution containing the oligomers OLG3, OLG4, and OLG5. The descent cycle was then continued until it reached 22° C. Subsequently, 5 units (5 μl) of T4 ligase (Boehringer Mannheim, Indianapolis, Ind.) and 45 μl of manufacturer's 10× T4 DNA ligation buffer (Boehinger Mannheim, Indianapolis, Ind.) was added, and ligation proceeded overnight at 10° C.

The ligated DNA was precipitated with 2 volumes of 100% ethanol and incubated at −70° C. for 1 hour. The precipitate was centrifuged for 30 minutes at 17000×g at 4° C. The supernatant was discarded and pellet was washed with 1 ml of 70% ethanol and centrifuged for 10 minutes at 17000×g at 4° C. The DNA pellet was dried under vacuum (Speed vac evaporator; Savant Inc.) and resuspended in 45 μl sterile double distilled water.

DNA of the correct molecular weight was isolated by electrophoresis. 5 μl of 10× loading buffer (6.25 g Ficoll and 0.93 g Disodium EDTA/25 ml 10% SDS, Orange G, Xylene Cyanole, and Bromophenol Blue) was added to the sample and loaded onto a 14.5 cm×16 cm×0.15 mm urea/acrylamide gel (7M urea/8% acrylamide with 1.1% Bis). TBE (89 mM Tris, 89 mM Boric acid, and 2 mM EDTA pH8.0) was used as both gel and electrophoresis buffer. The sample was electrophoresed at 35 mA until the Orange G dye line had migrated within 1 cm of the bottom of the gel. The acrylamide gel was washed twice with water for 5 minutes. After the last wash, the gel was incubated for 3 minutes in a 500 ml solution containing 10 ul of 10 mg/ml of ethidium bromide, and visualized under a UV-light source. The band corresponding to the ligated DNA was excised and cut into small pieces for electroelution in an IBI electroelutor apparatus (Model UEA: International Biotechnologies Inc., New Haven, Conn.).

For electroelution, the salt trap of the apparatus was filled with 125 μl of 7M sodium acetate/bromophenol blue dye solution. The buffer chamber was filled with ½× TBE. The sample was electroeluted for 1 hour at 85V. After removing the eluted DNA, the sample well was washed with ½× TBE and combined with the initial eluate. The eluted DNA was then precipitated overnight at −70° C. with 2 volumes of 100% ethanol. The precipitate was pelleted, washed as previously described, and resuspended in 15 ul of sterile double distilled water.

Preceding the ligation of the eluted partial PLP gene to the pRc/CMV vector (Invitrogen, San Diego, Calif.), the pRc/CMV vector construct was cut with the restriction endonucleases Apa I and Hind III according to the Manufacturer's instructions (Boehringer Mannheim, Indianapolis, Ind.). The resuspended PLP gene construct was then added to a 5 µl mixture containing 0.3 µg of pRc/CMV cut vector (2 µl), 1 unit T4 ligase (1 µl) (Boehringer Mannheim, Indianapolis, Ind.), and 2 µl of Manufacturer's 10× T4 DNA ligation buffer (Boehringer Mannheim, Indianapolis, Ind.). The ligated vector was then transformed into the competent cell line AG1.

Transformation proceeded by combining the ligation mixture with the AG1 cells and incubating it on ice for 20 minutes. The cell/vector mixture was then incubated at 42° for 2 minutes and plated overnight onto a Luria Broth agar (LB; Bio101, Vista, Calif.) plate, supplemented with 80 mg/ml of ampicillin (Sigma, St. Louis Mo.) Colonies were screened for the correct sequence vector by first isolating the plasmid DNA and then sequencing the DNA.

To isolate the plasmid, a commercially available plasmid purification kit, Wizard Minipreps (Promega, Madison, Wis.) was used. Colonies were picked from the LB/Amp plates and grown for 3.5 hours in 5 ml of LB medium (BIO 101, Vista, Calif.) supplemented with 80 mg/ml of ampicillin (Sigma, St. Louis, Mo.). 3 ml of the medium was centrifuged at 17000×g at room temperature, for 1 minute to pellet the cells. Isolation of the plasmid proceeded according to the Manufacturer's instructions. 1 µg of the isolated DNA was used for sequencing.

The oligonucleotide sequence can be checked by methods well known in the art, such as that described by Sanger et. al., *PNAS U.S.A.* 70:1209 (1973) or by the Maxam-Gilbert method, *Meth. Enzymology*, 65:499 (1977), the disclosures of both of which are incorporated herein by reference. Preferably, the plasmid can be sequenced using an automated DNA sequencer. For the PLP pRc/CMV construct, the plasmid was sequenced using automated fluorescent DNA sequencing procedures (Perkin Elmer/Applied Biosystems Inc, Foster City, Calif.) using the following primers: GATT-TAGGTGACACTATAG and TAATACGACTCACTAT-AGGG. These primers primed off the vector, which flanked the Kozak and "stop" site of the total construct. FIG. 1 shows a map of the partial PLP gene showing the sequence of the gene product and restriction sites. At the 5' end of the construct we had previously inserted a hydrophobic leader sequence from the MHC class I $L^d$ gene to enable the gene product to be synthesized in the endoplasmic reticulum (ER) for later constitutive secretion. Linsk et al. *J. Exp. Med.* 164:794–813 (1996). In addition, a lysine codon at the 3' end was added to ensure that the protein could not be retained in membrane. A Kozak box was included in the construct to ensure efficient translation. Restriction sites Afl II and BamHI were included in the construct to allow for insertion of further epitopes.

EXAMPLE 2

IN VITRO EXPRESSION OF THE PLP PROTEIN

The following experiments were performed in order to demonstrate that the PLP vector encodes a protein which is constitutively secreted. Specifically, the mRNA levels of PLP were evaluated in SJL fibroblast cells transfected with the pRc/CMV-PLP vector, and mRNA and protein levels of PLP were evaluated in SJL fibroblast cells transfected with the pG1PLPSvNa vector.

1. Establishment of Fibroblast Cultures

Syngeneic fibroblasts (derived from SJL mice) were obtained from Dr. G. Dveskler (Uniformed Services University, Bethesda, Md.) and expanded at 37° incubation using DMEM growth medium, supplemented with 5% glutamine and 10% FCS. The cells were harvested and frozen at $1\times10^7$ cells per vial, and aliquots were quality control tested for mycoplasma, sterility and viability.

2. Retroviral Constructs

Figure 2A:
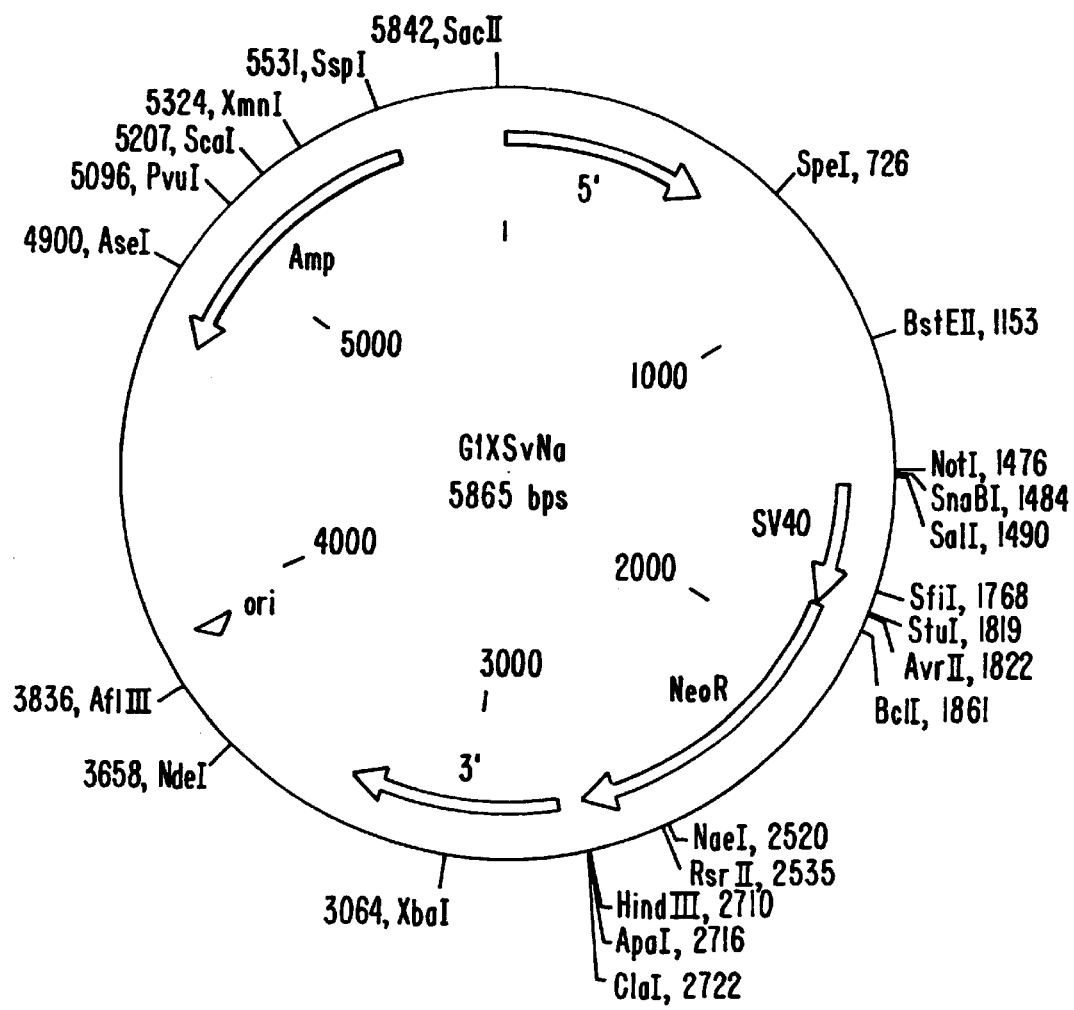
FIGS. 2(A+B) is a map of the G1XSvNa vector illustrating restriction sites and functional features.
FIG. 2b illustrates the entire DNA sequence of G1XSvNa.
Figure 3:
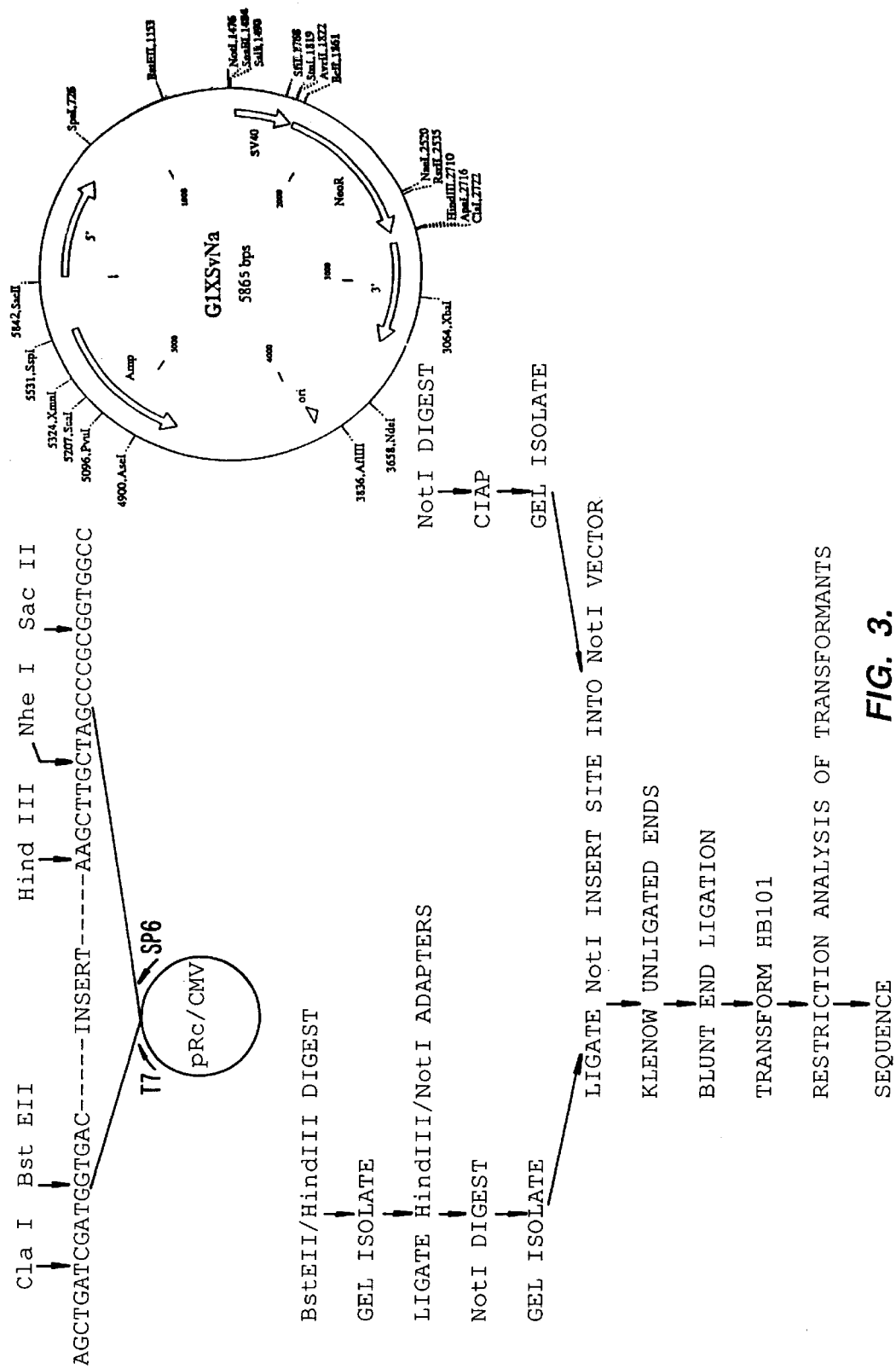
FIG. 3 outlines the method of constructing a G1XSvNa vector containing the PLP gene insert.

A recombinant retroviral vector in which exogenous genes are inserted into a retroviral vector was constructed. The cloning strategy was to construct a pGlXSvNa vector (W. French Anderson, University of Southern California) containing the PLP insert from pRc/CMV-PLP. The pG1XSvNa vector, like most retroviral vectors used in preclinical and clinical trials, is derived from the Moloney murine leukemia retrovirus (Mo-MLV). Rosenberg et al., *N. Eng. J. Med.* 323:570–578 (1990), Culver et al., *Science* 256:1550–1552 (1992). The G1XSvNa vector is a 5865 bp vector whose map, functional features and complete DNA sequence are shown in FIGS. 2a and 2b. FIG. 3 illustrates the procedure for constructing the pG1PLPSvNa vector. Essentially, the pRc/CMV-PLP vector was digested with BstEII/HindIII and PLP encoding fragment was isolated by gel electrophoresis. After electroelution, HindIII/NotI adapters (Stratagene, La Jolla, Calif.) were ligated into the HindIII site of the eluted fragment. A NotI digestion was performed to generate NotI ends. A NotI digest was performed on pG1XSvNa and the 5865 bp fragment was isolated, electroeluted, and a CIAP (Calf intestine alkaline phosphatase treatment) was performed on the fragment ends. The NotI site of the insert was ligated into the NotI site of the vector. BstEII ends of the insert and NotI site of the vector were Klenowed. A blunt end ligation is performed to close the vector. HB101 cells were transformed with ligation mix and restriction analysis was performed to determine which vectors contain insert and the insert orientation. The recombinant retroviruses are non-replicating and incapable of producing infectious virus.

3. Retroviral Vector Supernatant

To prepare supernatant containing PLP-recombinant retrovirus, the PLP-transduced retroviral packaging cell line PA317 was grown in 4 ml of appropriate culture medium in a T25 flask (Corning, Cambridge, Mass.). Retroviral vector supernatant is produced by harvesting the cell culture medium when cells were 80–90% confluent, and stored in 1 ml aliquots at −70° C.

The following tests were performed on the PLP cell line and/or the vector supernatants:

(1) The viral titer is determined using 3T3 cells. Viral preparations with titers greater than $5\times10^4$ colony forming units/ml are used.

(2) Sterility of the producer cell line and the supernatant is assured by testing for aerobic and anaerobic bacteria, fungus and mycoplasma.

The PLP-vector preparations from PA317 can be extensively tested to assure that no detectable replication competent virus is present. This is particularly relevant to the embodiment of the invention wherein the invention is used to treat humans. Tests on both the viral supernatant and on the transduced fibroblasts can be performed to determine if there is replication competent virus present. The following tests can be performed on the producer cell line and/or the viral supernatant:

(1) The viral titer is determined using 3T3 cells. Viral preparations with titers greater than $5\times10^4$ colony forming units/ml are used.

(2) Southern blots are run on the producer cell line to detect the partial PLP gene.

(3) PLP production by the producer cell line is measured and should be significantly above baseline control values, as determined by ELISA assay.

(4) Sterility of the producer cell line and the supernatant is assured by testing for aerobic and anaerobic bacteria, fungus and mycoplasma.

(5) Viral testing is performed including: MAP test, LCM virus, thymic agent, S+L-assay for ecotropic virus, S+L assay for xenotropic virus, S+L-assay for amphotropic virus and 3T3 amplification.

(6) Electron microscopy is performed to assure the absence of adventitious agents.

Following the introduction of the gene into fibroblasts, the following tests are performed on the fibroblasts prior to administration to patients.

(1) Cell viability is greater than 70% as tested by trypan blue dye exclusion.

(2) Cytologic analysis is performed on over 200 cells prior to infusion to assure that tumor cells are absent.

(3) Sterility is assured by testing for aerobic and anaerobic bacteria, fungus and mycoplasma.

(4) S+L-assay including 3T3 amplification must be negative.

(5) PCR assay for the absence of 4070A envelope gene must be negative.

(6) Reverse transcriptase assay must be negative.

(7) Southern blots run on the transduced fibroblasts to assure that intact provirus is present.

(8) PLP protein assay to assure the production of PLP protein.

4. Transfection of Fibroblasts

Prior to the transfection of the SJL fibroblasts, highly purified PLP-pRc/CMV vector was isolated from the transformed AG1 cells. Large scale purification was performed by using a commercially available kit and CsCl gradient banding. Initial purification was accomplished using a Wizard Megaprep Kit (Promega, Madison, Wis.). A 1000 ml culture of transformed AG1 cells, grown overnight in LB/Amp at 37° C., was pelleted and the plasmid DNA isolated according to the Manufacturer's instructions. The isolated DNA, which was suspended in 3 ml of TE buffer (10 mM Tris-HCl, pH 7.4, and 1 mM disodium EDTA, pH, 8.0) was further processed by CsCl gradient banding. A modified CsCl banding of the DNA was performed based on procedures found in "Current Protocols in Molecular Biology, Vol 1" (Greene Publishing Associates and Wiley-Interscience).

After the DNA band was extracted from the ultracentrifuge tubes, ethidium bromide was removed from the sample by washing it with 3 volumes of SSC saturated isopropanol. The wash was repeated until the aqueous layer appeared clear. CsCl was removed by precipitation. 2 volumes of 0.2M NaCl/TE and 2 volumes of 100% ethanol (relative to the combined total volume of DNA solution and 0.2M NaCl/TE) were added to the sample, mixed and placed on ice for 10 minutes. The precipitated DNA was pelleted by centrifugation at 10000×g for 10 minutes at 4° C. The pellet was washed with cold 70% ethanol, recentrifuged at 10000×g for 10 minutes at 4° C., and dried under vacuum (Speed vac evaporator; Savant Inc.). The purified DNA was resuspended with double-distilled sterile water and utilized in the transfection process.

Test SJL fibroblasts were transfected using LipofectAMINE Reagent (Life Technologies Inc./Gibco BRL) according to the manufacturer's instructions. Control SJL fibroblasts underwent the same procedure without the presence of a DNA construct. 3 $\mu$g of CsCl purified PLP-pRc/CMV plasmid and 25 $\mu$l of Lipofectamine were used for transfection. Approximately 3×10$^5$ SJL cells, seeded overnight into 25 cm$^2$ culture flasks (Corning Costar Corp., Cambridge, Mass.) and grown at 37° with 5% $CO_2$ in 5 ml of DMEM culture medium (Dulbecco's Modified Eagle's Medium (Irvine Scientific, Santa Ana, Calif.), supplemented with 5% glutamine, 10% Fetal Calf Serum, 25 Units/ml of penicillin G sodium, and 25 $\mu$g/ml of streptomycin sulfate, were washed with 3 ml serum free HL-1 medium (Hycor Biomedical Inc., Irvine, Calif.). After the DNA/lipofectamine complexes were incubated with cells for 6 hours at 37° with 5% $Co_2$, 1 ml of DMEM was added to the flasks. The flasks were incubated overnight at 37° with 5% $CO_2$. The medium was replaced with 5 ml of fresh DMEM the next morning. 36 hours after the end of the transfection period, the medium was replaced with 5 ml of DMEM containing 900 $\mu$g of G418 (Life Technologies Inc./Gibco BRL)/ml of medium. The test cells were grown in the presence of 900 $\mu$g of G418 of medium until all the control cells had died; and no more cell death could be observed in the test sample flask. The G418 concentration was then reduced to 600 $\mu$g/ml of culture medium for duration of cell culturing procedures.

5. Transduction of Fibroblasts

Retroviral constructs containing a neo-selectable marker together with either the PLP gene or the Lac-z gene were used to transduce fibroblasts. Transduction with the retrovirus was performed on healthy cells (90% viable, as determined by trypan blue staining). 2×10$^6$ cells were plated in 0.5 ml DMEM-10 media (DMEM media supplemented with 10% fetal calf serum, 2 mM L-glutamine, 50 U/ml penicillin G, 50 mg/ml streptomycin in one well of a 24-well plate (Falcon, Franklin Lakes, N.J.). Cells were placed in the incubator and allowed to settle (37°, 5% $CO_2$). After cells had settled, 1 ml of retroviral supernatant and polybrene (Sigma, St. Louis, Mo.) (final concentration 10 $\mu$g/ml) was added to the well. Cells were incubated as above for 2.5 hours without shaking. After 2.5 hours, cells were transferred to a T25 flask and DMEM-10 media was added to a total volume of 8 ml. Selection media (culture media comprising DMEM-10 supplemented with 900 $\mu$g/ml G418 (Gibco, Grand Island, N.Y.) was added on the third day after transduction. The G418 concentration was then reduced to 600 $\mu$g/ml of culture medium for the duration of cell culturing procedures.

6. mRNA Expression Analysis mRNA isolation was performed using aseptic techniques, RNAse free supplies, and DEPC (Diethylpyrocarbonate) treated solutions. 4×10$^6$ experimental and control SJL cells were washed twice with cold Phosphate-buffered saline, resuspended in 200 $\mu$l cell lysis mix (10 mM TRIS pH 7.5, 0.15M NaCl, 1.5 mM $MgCl_2$, 0.65% NP 40), vortexed, and centrifuged at 17000×g at 4° for 5 minutes. The supernatant was transferred to a tube containing 200 $\mu$l of urea mix (7M urea, 1% SDS, 0.35M NaCl, 10 mM EDTA, and 10 mM Tris-HCL, pH 7.5) and 400 $\mu$l of phenol:chloroform;isoamyl alcohol (25:24:1). The solution was vortexed and centrifuged for 1 minute at 17000×g. This procedure was repeated twice using the aqueous layer and then transferred to a tube containing 400 $\mu$l of phenol and washed as before. The aqueous layer was transferred again to another tube, and precipitated with 1 ml of 100% ethanol overnight at −20° C. The precipitated RNA was washed with 1 ml 70% ethanol. After the ethanol was discarded, the pellet was dried under vacuum. 1 $\mu$g of the RNA was used for RT-PCR analysis.

RT-PCR was performed using a commercially available kit, GeneAmp RNA PCR Kit (Perkin Elmer/ABI) according to the Manufacturer's instructions. The following primers were used to amplify the cDNA: 5'-GCGACTACAAGACCACCATCT-3' and 5'-TAAGGCTAGCATAGGTGATG-3'. The PCR products were electrophoresed on a 1.5% agarose (SeaKem GTG; FMC)/TAE gel with 1 $\mu$l of 10 mg/ml of ethidium bromide/ml of agarose solution. The gel was electrophoresed using TAE buffer at a constant 40 mA. Electrophoresis was continued until the molecular weight marker bands had separated adequately enough, to verify the PCR products' approximate molecular size. The DNA band of interest was then excised and gel purified, using the commercially available MERmaid Kit (Bio 101, Vista, Calif.), according to the Manufacturer's instructions. The purified DNA was then sequenced by automated Fluorescent DNA sequencing procedures (Perkin Elmer/ABI, Foster City, Calif.).

Figure 4:
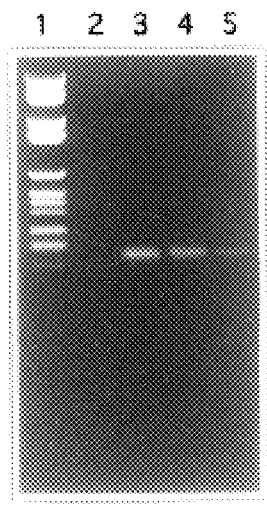
FIG. 4 shows the level of mRNA expressed in transfected and transduced SJL fibroblast cells as detected by reverse transcriptase PCR. Lane 1 is molecular weight standards, Lane 2 is Negative control from mock transfection, Lane 3 is positive control-PLP-gene plasmid, Lane 4 is cDNA from PLP-transfected SJL fibroblasts, Lane 5 is cDNA from PLP transduced SJL fibroblasts.

FIG. 4 is an agarose gel showing PLP-specific RT-PCR products. The data illustrates that mRNA is present in both PLP-transduced and PLP-transfected cells. The correlation between mRNA and secreted protein remains to be determined since peptide concentration does not necessarily correspond to the level of mRNA.

7. Protein Expression Analysis

The in vitro qualitative expression of the proteins encoded by the PLP gene was detected immunologically by ELISA. Undiluted supernatants from cultures of fibroblasts transduced with the PLP gene were tested. Wells of 96 microtiter plate were coated with the supernatants. Primary anti-PLP-antibody 4E10 139–151, from Dr. M. Lees (Harvard), is specific for PLP 139–151 and was added to wells as undiluted hybridoma supernatant followed by horseradish peroxidase (HRP)-conjugated goat anti-mouse secondary antibody in a concentration of 1:500. The plate was developed and analyzed at 490 nm on a microplate reader. FIG. 5 illustrates the results of ELISA assays on transduced fibroblast supernatants. Samples 1 and 2 were PLP (amino acids 139–151) and HIV gp120 peptides used at a concentration of 5 ug/ml. This experiment illustrates that the transduced PLP-transduced fibroblasts do produce and secrete the partial PLP protein.

EXAMPLE 3

IN VIVO EFFECTS OF THE PLP PROTEIN

Critical to the success of this invention in the embodiment of this example is the ability to deliver genetically manipulated fibroblasts to patients so that the cells survive in sufficient numbers and for long periods of time, in order that continuous secreted antigen may be provided to the patient.

To assess the fate of transplanted transduced fibroblasts, SJL fibroblasts transduced with retrovirus encoding B-galactosidase were injected subcutaneously between the shoulders of SJL mice. All mice were female mice of the SJL strain between 6–8 weeks old and were obtained from Jackson Labs. Animals were housed and maintained according to NIH guidelines (National Research Council, 1986). These fibroblasts survived in large numbers after 60 days. Fibroblasts injected into the footpad or intramuscularly could not be detected at eight days.

1. In Vivo Fate B-gal Transduced Cells

Figure 6:
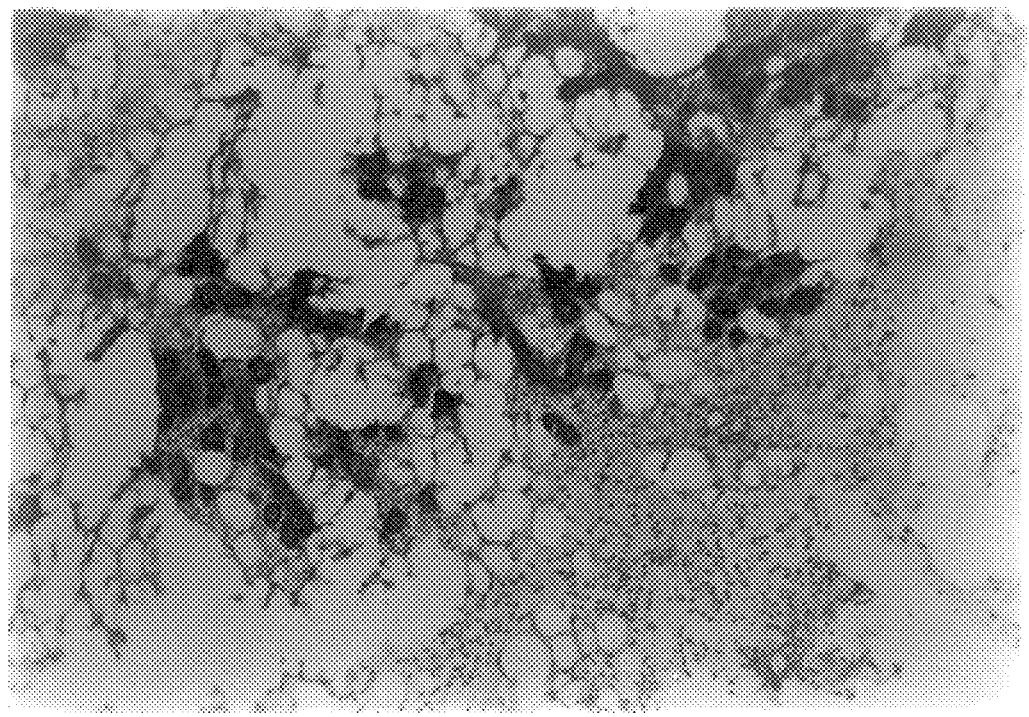
FIG. 6 demonstrates the level of B-Gal expression in transduced fibroblasts.

The activity of the B-Galactosidase marker was evaluated using two groups of eight normal mice. Two mice were injected subcutaneously on the back, two mice were injected intramuscularly and two mice were injected in the footpad with Lac-Z transduced cells. One animal was injected with fibroblasts transduced with neo-marker only, and the last mouse was injected with untransduced fibroblasts. After harvesting and washing, the different cell lineages were suspended in a concentration of $10^7$ cells in 0.2 ml of Hank's PBS and slowly injected using a 25 gauge needle at different sites. Animals were sacrificed at 10 and 15 days post treatment and injection sites were submitted to histochemical study. Pieces of tissue were fixed in 4% paraformaldehyde for one hour, washed in PBS three times and then kept in 8.4% acrylamide solution overnight. The next morning tissues were embedded in acrylamide which after hardening were cut and frozen. The frozen sections were done in 10 um by cryostat and stained with 1 ml of 5-Bromo-4-chloro-3-indolyl-B-d-galactopyranoside (X-Gal) in PBS. The X-Gal was dissolved in DMSO at 40 mg/ml and then added to the reaction mixture. Incubation was for 14–18 h at 37°. FIG. 6 illustrates B-Gal expression in transduced fibroblasts 60 days in vivo. There was no evidence of an inflammatory response, suggesting that the retrovirus used to transduce syngeneic fibroblasts, does not evoke an immune response or rejection process.

2. Effect of PLP in Normal SJL Mice

Another important aspect of this invention in the embodiment of this example is determining whether transduced fibroblasts secreting PLP actually produce EAE in normal animals. To test this, $10^7$ PLP-secreting SJL fibroblasts were injected into 12 normal SJL mice. Six animals had fibroblasts placed subcutaneously and six animals had fibroblasts injected intraperitoneally. Animals were sacrificed at day 16 and showed no evidence of inflammatory disease or EAE. FIG. 7 illustrates the clinical scoring system for chronic EAE. Y-A Lu et al., *Mol. Immunol.* 28:623–630 (1991), J. Williamson et al., *J. Neuroimmunol.* 32:199–207 (1991). In the EAE model for multiple sclerosis, using spinal cord homogenates plus adjuvant, inflammation in the CNS can be seen by day 14. In this study, normal animals injected with PLP-secreting SJL fibroblasts did not show any signs of clinical disease even at day 60. In addition, the animals did not show any histologic evidence of inflammation in the CNS at day 60. FIG. 8 illustrates the histological scoring system for EAE. J. Governman et al., *Cell* 72:551–560 (1993).

3. Clinical and Histological Assessment of Acute EAE Mice Treated with Retrovirus Transduced Fibroblasts.

Six week SJL mice were infected with mouse spinal cord homogenate (MSCH) in complete Freund's Adjuvant (CFA) and with MSCH in incomplete Freund's Adjuvant IFA, seven days later. *J. Immunol.* 144:909–915 (1990). The initial EAE attack was observed on days 14–18, with full recovery by 21. Ninety-five percent of animals showed clinical evidence of an acute attack and these were given either $10^7$ PLP secreting SJL fibroblasts or control fibroblasts on day 21. Animals not showing clinical disease were eliminated from the experiment. FIG. 9 illustrates the clinical assessment of EAE mice treated with retrovirus transduced fibroblasts. Animals receiving the PLP secreting fibroblasts had a marked reduction of clinical signs and had dramatic reduction in inflammatory cells, particularly in the brain. FIG. 10a illustrates the pathologic assessment of brain and spinal cord of SJL mice treated with retrovirus transduced fibroblasts. FIG. 10b is a summary of the pathologic assessment of brain and spinal cord from days 55–60 and 90–95. Histological assessment of EAE Grades in Brain and Spinal Cord were performed following the preparation of hematoxylin and eosin stained sections.

4. Clinical and Histological Assessment of Chronic EAE Mice Treated with Retrovirus Transduced Fibroblasts.

150 mice were inoculated with MSCH in CFA. A second immunization was given 7 days later. A. M. Brown and D. E. McFarlin, *Laboratory Invest.* 45:278–284 (1981). On day +14 to 16, 113 animals developed clinical disease lasting 3–4 days. These positive animals were separated for subsequent experiments and had their first relapse on day +55 to 60, with 100 animals becoming sick. These were again separated and on day +137, 67 had a relapse. Eight days after relapse, animals were each transplanted with $10^7$ fibroblasts and then sacrificed 18 to 23 days later. Four different types of fibroblasts were used, those transduced with retrovirus encoding PLP, encoding B-galactosidase and encoding neo-selectable marker as well as untransduced cells. FIG. 11 shows the histology of SJL mice with chronic EAE treated with retrovirus transduced fibroblasts. There were no animals receiving PLP secreting fibroblasts with 2+ to 3+ inflammation.

5. Peripheral Immune Status of Treated Mice V. Control EAE Mice.

Spleen cells from our EAE control mice and from four EAE mice which had been treated with fibroblasts expressing the PLP protein were used in proliferation assays, in which they were incubated with 40 $\mu$M PLP peptide 139–151 or 40 $\mu$M HIV gp120 peptide 308–322 for 4 days and then pulsed with $^3$H-thymidine for 24 hours.

Briefly, animals were sacrificed by $CO_2$ asphyxiation. Spleen cells were dispersed to single cell suspensions in RPMI 1640 by passing through a size 60 mesh, and washed once before being cultured (8×10$^5$ per well) in 0.2 ml of HL-1 medium (Hycor Biomedical, Irvine, Calif.), supplemented with 2 mM glutamine, 100 U/ml penicillin, 100 $\mu$g streptomycin either alone or with 40 $\mu$M of peptide in 96-well tissue culture plates for 4 days at 37° C. with 5% $CO_2$. PLP peptide 140–151 and MBP peptide 89–101 were used for antigen-specific proliferation while HIV gp120 peptide 308–322 was used as negative control. Where indicated, some wells also contained 10 U/ml of recombinant mouse IL-2 (Boehringer Mannheim, Indianapolis, Ind.). During the last 18–24 h of culture, each well was pulsed with 1 $\mu$Ci of $^3$H-thymidine (ICN, Irvine, Calif.), harvested onto 'Xtal Scint' glass fiber filters (Beckman, Fullerton, Calif.) and counted using a Beckman LS6000 Scintillation counter. Thymidine incorporation values (experimental counts per minute—background counts per minute) were calculated and represent means of triplicate cultures±standard deviation.

Figure 12A:
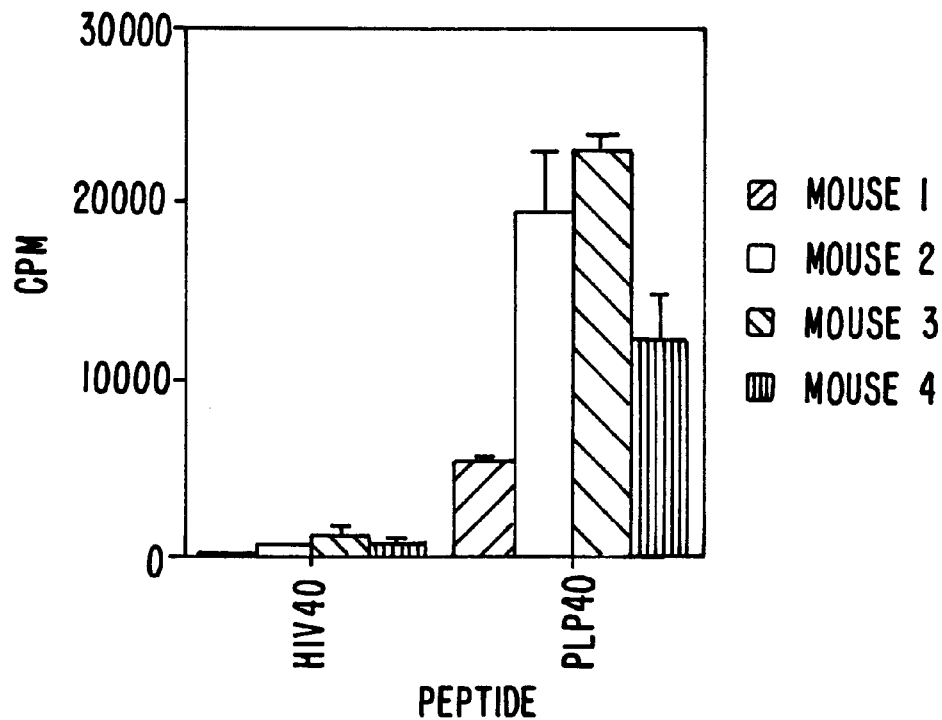
FIGS. 12(A+B) illustrates the results of proliferation assays using EAE mice treated with PLP-expressing fibroblasts.
Figure 12B:
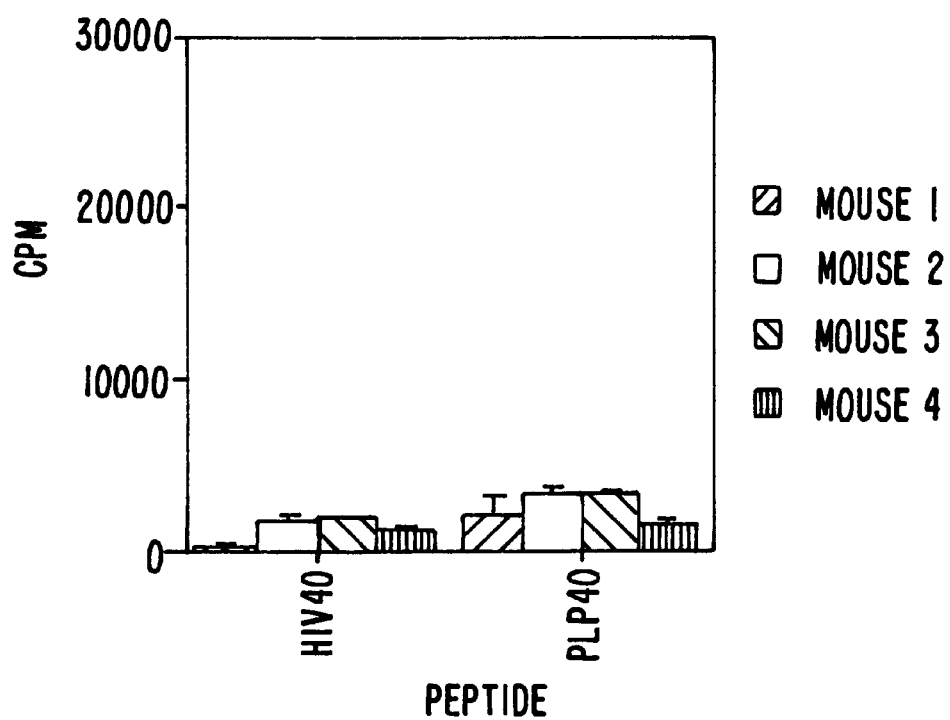

The results are shown in FIG. 12 and suggest that PLP specific proliferative responses are reduced significantly in EAE mice which have received PLP expressing fibroblasts.

Figure 13A:
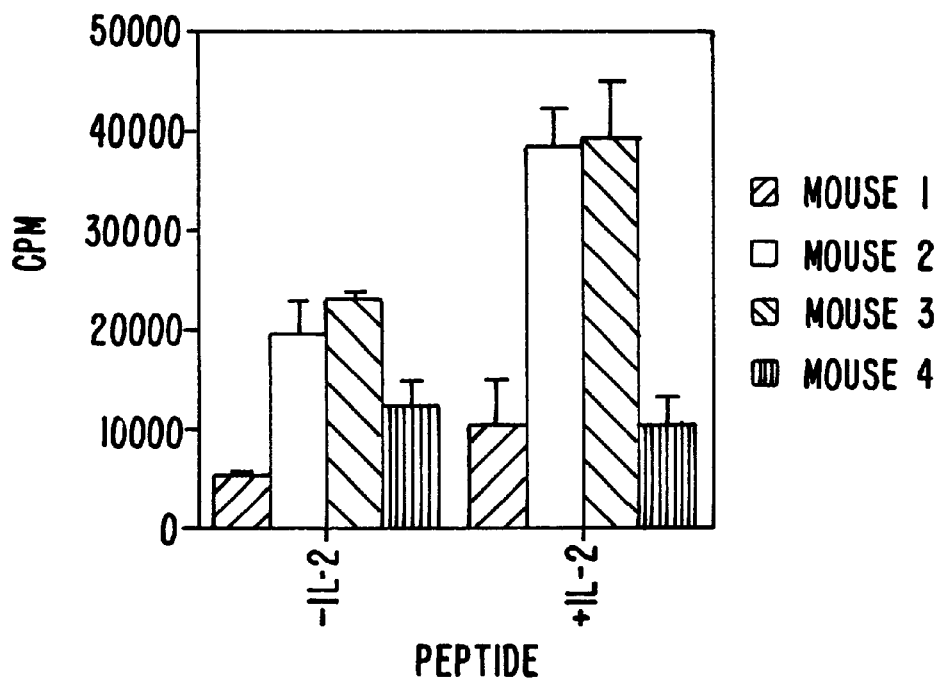
FIGS. 13(A+B) illustrates the results of proliferation assays with and without IL-2 using EAE mice treated with PLP-expressing fibroblasts.
Figure 13B:
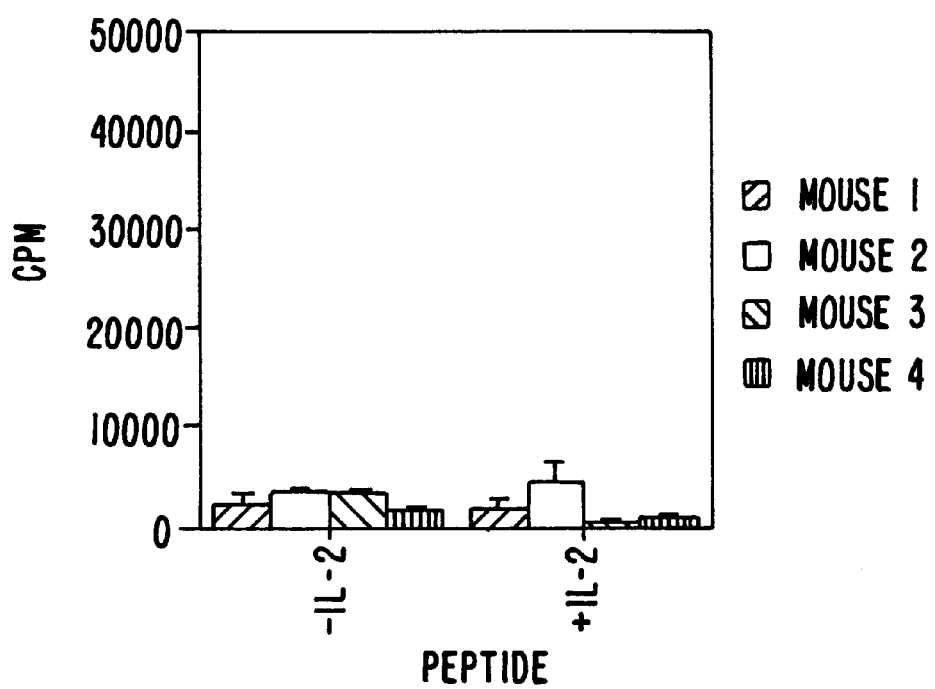

FIG. 13 illustrates the same experiment as in FIG. 12 but with the addition of mouse IL-2 (10 U/ml) for 5 days. These results illustrate that the mechanism by which the PLP specific proliferative responses are reduced significantly may suggest the possibility of deletion of T cells rather than anergy because these lymphocytes do not respond to IL-2.

Although the mechanism by which the present invention acts to restore tolerance in individuals suffering from T-cell mediated autoimmune disease is not entirely understood, the benefits of the treatment are clearly advantageous over alternative treatments. The method is a genetic approach to immunospecifically silence pathogenic T-cell responses and does not down-regulate the entire immune system. In the case where an individual with a T-cell mediated autoimmune disease exhibits pathogenic T-cells of multiple specificities, the invention may easily be adapted to target those specificities. For example, DNA encoding multiple self-antigenic epitopes may be introduced into the patient's cells. The invention is also advantageous in that the reagents can easily be made or obtained in sufficient quantity to carry out the invention.

The present invention is not to be limited in scope by the exemplified embodiments disclosed herein which are intended as illustrations of single aspects of the invention, and clones, DNA or amino acid sequences which are functionally equivalent are within the scope of the invention. Various modifications of the invention, in addition to those shown and described herein, will become apparent to those skilled in the art from the foregoing description. Such modifications are intended to fall within the scope of the appended claims.

Various publications are cited herein that are hereby incorporated by reference in their entireties.

What is claimed is:

1. A method of treating a patient for multiple sclerosis comprising: introducing autologous mammalian cells into a patient, said cells having been treated ex vivo to insert therein a poltnucleotide encoding one or more antigenic proteins which comprises an encephalogenic amino acid epitope sequence from a myelin protein, wherein said autologous mammalian cells express in vivo in said patient a therapeutically effective amount of said antigen protein or proteins to induce T cell tolerance to the expressed encephalogenic amino acid sequence from a myelin protein.

2. The method of claim 1 wherein said patient is human.

3. The method of claim 2 wherein said cells are fibroblast cells.

4. The method of claim 1 wherein said DNA segment has been inserted into said cells in vitro by a recombinant vector.

5. The method of claim 1 wherein said DNA segment has been inserted into said cells in vitro by a viral vector.

6. The method of claim 5 wherein said viral vector is a retroviral vector.

7. The method of claim 1 wherein said myelin protein is selected from the group consisting of myelin basic protein, proteolipid protein, and myelin-oligodendrocyte glycoprotein.

8. The method of claim 2 wherein said myelin protein is selected from the group consisting of myelin basic protein, proteolipid protein, and myelin-oligodendrocyte glycoprotein.

9. The method of claim 3 wherein said myelin protein is selected from the group consisting of myelin basic protein, proteolipid protein, and myelin-oligodendrocyte glycoprotein.

10. The method of claim 4 wherein said myelin protein is selected from the group consisting of myelin basic protein, proteolipid protein, and myelin-oligodendrocyte glycoprotein.

11. The method of claim 5 wherein said myelin protein is selected from the group consisting of myelin basic protein, proteolipid protein, and myelin-oligodendrocyte glycoprotein.

12. The method of any one of claims 1–3 or 7–11 wherein said antigenic protein additionally comprises a hydrophobic leader sequence, said hydrophobic leader sequence enabling the gene product to be synthesized in an endoplasmic reticulum for later constitutive secretion.

13. The process of any one of claims 1–3 or 7–11 wherein said polynucleotide further comprises a Kozak box, said Kozak box permitting efficient translation of an mRNA transcribed from said polynucleotide.

14. The process of any one of claims 1–3 or 7–11 wherein said polynucleotide further comprises a codon corresponding to a charged amino acid at the carboxyl terminus of said antigenic protein to ensure that the protein is not retained in membrane.

15. The process of any one of claims 1–3 or 7–11 wherein said polynucleotide further comprises one or more restriction sites to permit insertion of additional DNA sequences.

16. The process of any one of claims 1–3 or 7–11 wherein said polynucleotide further comprises a sequence encoding amino acids 101–157 of proteolipid protein.

17. A method of treating a human patient for multiple sclerosis comprising:

introducing autologous fibroblast cells into said human patient, said autologous fibroblast cells having been treated ex vivo to insert therein a polynucleotide comprising a recombinant retroviral vector which comprises an encephalogenic epitope sequence encoding amino acids 101–157 of proteolipid protein residues 27–83 of SEQ ID NO:2, a codon corresponding to a charged amino acid at the carboxyl terminus of said proteolipid protein to ensure that the protein is not retained in the membranes, a hydrophobic leader sequence which enables said amino acids 101–157 of proteolipid protein residues 27–83 of SEQ ID NO:2 to be synthesized into the endoplasmic reticulum of said autologous fibroblast cells for later constitutive secretion, a Kozak box permitting efficient translation of mRNA transcribed from said polynucleotide, and one or more restriction sites to permit insertion of additional gene sequences, whereby the gene product or gene products of said polynucleotide are expressed by said autologous fibroblast cells in said human in a therapeutically effective amount to induce T cell tolerance to said expressed encephalogelic epitope.

18. An engineered cell comprising a polynucleotide encoding a peptide which comprises an encephalogenic epitope from a myelin protein, wherein said peptide further comprises a positively charged residue at the carboxy terminus, wherein said peptide is secreted, and wherein said polynucleotide has been introduced into the cell by means of a recombinant vector.

19. The engineered cell of claim 18 wherein the encephalogenic epitope is from proteolipid protein, myelin basic protein, or myelin-oligodendrocyte glycoprotein.

20. The engineered cell of claim 19 wherein said peptide further comprises a hydrophobic leader sequence.

21. The engineered cell of claim 20 wherein said encephalogenic epitope comprises amino acids 101–157 of proteolipid protein residues 27–83 of SEQ ID NO:2.

* * * * *